United States Patent [19]
Walker

[11] Patent Number: 5,972,339
[45] Date of Patent: Oct. 26, 1999

[54] METHOD OF ELICITING ANTI-HIV-1 HELPER T CELL RESPONSES

[75] Inventor: Bruce D. Walker, Milton, Mass.

[73] Assignee: The General Hospital Corporation, Boston, Mass.

[21] Appl. No.: 08/969,721

[22] Filed: Nov. 13, 1997

[51] Int. Cl.[6] .................................................. A01N 65/00
[52] U.S. Cl. .................................... 424/188.1; 424/208.1; 514/2; 530/324; 530/325; 530/326; 530/327; 530/328; 530/350
[58] Field of Search ........................ 514/2; 530/323–328, 530/826; 424/185.1–188.1, 204.1, 208.1, 278.1, 283.1

[56] References Cited

U.S. PATENT DOCUMENTS

| | | | |
|---|---|---|---|
| 4,943,628 | 7/1990 | Rosen et al. | 530/326 |
| 5,639,854 | 6/1997 | Sia et al. | 530/324 |

FOREIGN PATENT DOCUMENTS

| | | | |
|---|---|---|---|
| 0230222 | 7/1987 | European Pat. Off. | |
| WO 90/13564 | 11/1990 | WIPO | C07K 7/08 |
| WO 93/04697 | 3/1993 | WIPO | A61K 39/12 |
| WO 93/15205 | 8/1993 | WIPO | C12N 15/31 |
| WO 94/04171 | 3/1994 | WIPO | A61K 37/00 |

OTHER PUBLICATIONS

Autran et al., "Positive Effects of Combined Antiretroviral Therapy in CD4+T Cell Homeostasis and Function in Advanced HIV Disease", Science 277:112–116, 1997.
Battegay et al., "Enhanced Establishment of a Virus Carrier State in Adult CD4+ T Cell–Deficient Mice", Journal of Virology 68:4700–4704, 1994.
Berzofsky et al., "Antigenic Peptides Recognized by T Lymphocytes from AIDS Viral Envelop–immune Humans", Nature 334:706–708, 1988.
Connors et al., "HIV Infection Induces Changes in CD4+ T–Cell Phenotype and Depletions Within the CD4+ T–Cell Repertoire that are not Immediately Restored . . .", Nature Medicine 3:533–540, 1997.
Johnson et al., "HIV–1 gag–Specific Cytotoxic T Lymphocytes Recognize Multiple Highly Conserved Eptiopes", The Journal of Immunology 147:1512–1521, 1991.
Kelleher et al., "Alterations in the Immune Response of Human Immunodeficiency Virus (HIV)–Infected Subjects Treated with an HIV–Specific Protease Inhibitor, . . ."The Journal Infectious Diseases 173:321–329, 1996.
Lekutis et al., "HIV–1 env DNA Vaccine Administered to Rhesus Monkeys Elicits MHC Class II–Restricted CD4+ T Helper Cells That Secrete . . .", The Journal of Immunology pp. 4472–4477, 1977.
Matloubian et al., "CD4+ T Cells Are Required to Sustain CD8+ Cytotoxic T–Cell Responses During Chronic Viral Infection", Journal of Virology 68:8056–8063, 1994.
Planz et al., "A Critical Role for Neutralizing–antibody–producing B Cells, CD4+ T Cells, and Interferons in Persistent and Acute Infections of Mice . . . ", Proc. Natl. Acad. Sci. 94:6874–6879, 1997.
Schnittman et al., "Preliminary Evidence for Partial Restoration of Immune Function in HIV Type 1 Infection with Potent Antiretroviral Therapies: . . .", AIDS Research and Human Retroviruses 13:815–818, 1997.
Schrier et al., "T Cell Recongnition of HIV Synthetic Peptides in a Natural Infection", The Journal of Immunology 142:1166–1176, 1989.
Shearer et al., "Method for Detecting Immune Dysfunction in Asymptomatic AIDS (Acquired Immunodeficiency Syndrome) Patients and Other Conditions", U.S. Dept. of Commerce NTIS PB89–189997, 1989.
Thomsen et al., "Exhaustion of CTL Memory and Recrudescence of Viremia in Lymphocytic Choriomeningitis Virus–Infected MHC Class II–Deficient Mice . . .", The Journal of Immunology pp. 3074–3080, 1996.
Von Herrath et al., "CD4–Deficient Mice Have Reduced Levels of Memory Cytotoxic T Lymphocytes after Immunization and Show Diminished . . . ", Journal of Virology 70: 1072–1079, 1996.
Wahren et al., "Characteristics of Specific Cell–Mediated Immune Response in Human Immunodeficiency Virus Infection", Journal of Virology 61:2017–2023, 1987.
Walter et al., "Reconstitution of Cellular Immunity Against Cytomegalovirus in Recipients of Allogeneic Bone Marrow by Transfer of T–Cell Clones From the Donor", The New England Journal of Medicine 333:1038–1044, 1995.
Saunders Dictionary & Encyclopedia of Laboratory Medicine and Technology, edited by James Bennington, W.B. Saunders Co., Philadelphia, p. 30, 1984.
Harding et al. Cell, vol. 64(1991), pp. 393–401.

*Primary Examiner*—Jeffrey Stucker
*Attorney, Agent, or Firm*—Fish & Richardson P.C.

[57] ABSTRACT

A method of producing an HIV-specific helper T cell response in an animal by (1) providing a polypeptide 8 to 50 amino acid residues in length and having a helper T cell epitope of a HIV-1 p24 peptide; and (2) administering to the animal an amount of the polypeptide sufficient to produce an HIV-specific helper T cell response.

33 Claims, 13 Drawing Sheets

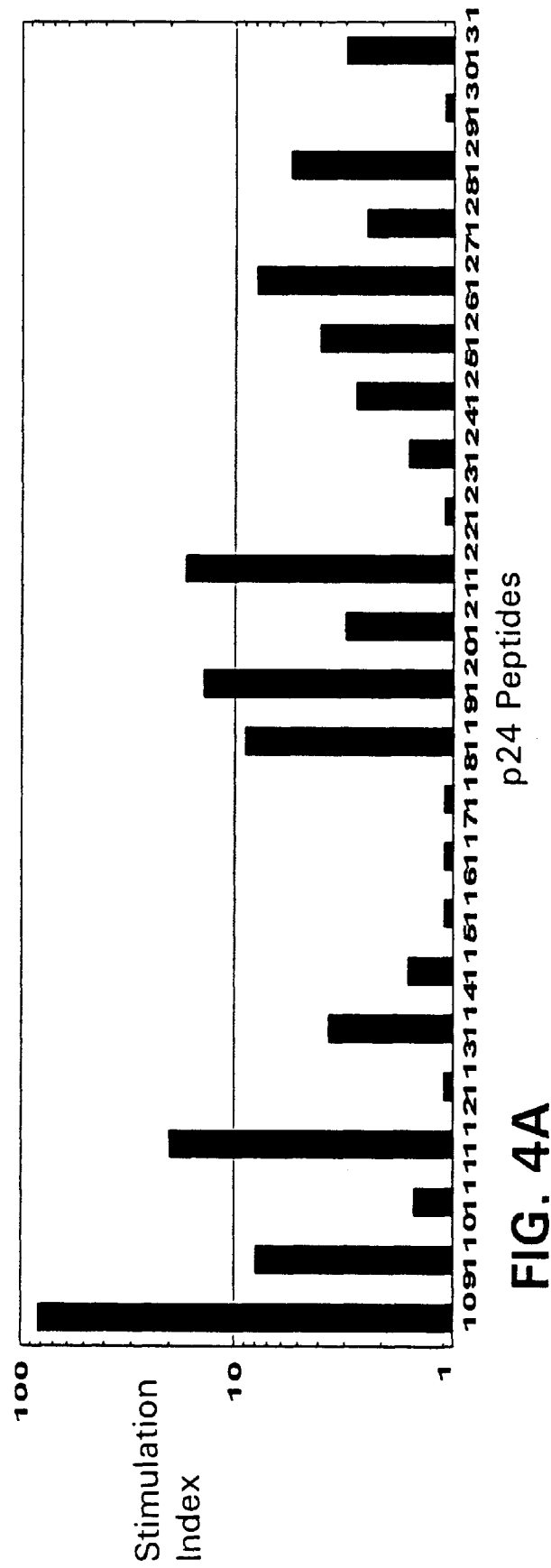

METHOD OF ELICITING ANTI-HIV-1 HELPER T CELL RESPONSES

STATEMENT AS TO FEDERALLY SPONSORED RESEARCH

This work was funded in part by National Institutes of Health grants F32-A109738, RO1-A136550, RO1-A128568, and U19-A136611. The Government has certain rights in the invention.

FIELD OF THE INVENTION

The field of the invention is therapy and prophylaxis for HIV infection.

BACKGROUND OF THE INVENTION

Major histocompatibility complex (MHC) molecules are cell surface receptors that present antigen to immune cells in vertebrates. MHC molecules are classified as class I and class II. In general, MHC class II-bearing cells present antigen to CD4+ helper T cells. Humans possess three distinct MHC class II isotypes: DR, for which approximately 70 different allotypes are known; DQ, for which 33 different allotypes are known; and DP, for which 47 different allotypes are known. Each individual bears two to four DR alleles, two DQ alleles, and two DP alleles.

MHC molecules (both class I and class II) participate in the obligate first step of immune recognition by binding small protein fragments (peptides) derived from pathogens or other non-host sources, and presenting these peptides to the regulatory cells (T cells) of the immune system. In the absence of MHC presentation, T cells are incapable of recognizing pathogenic material. Cells that express MHC class II receptors are termed antigen presenting cells (APC). APCs ingest pathogenic organisms and other foreign materials by enveloping them in endosomic vesicles, then subjecting them to enzymatic and chemical degradation. Foreign proteins which are ingested by APCs are partially degraded or "processed" to yield a mixture of peptides, some of which are bound by MHC class II molecules that are en route to the surface. Once on the cell surface, MHC-bound peptides are available for T cell recognition.

Infection with HIV-1 is characterized by a quantitative decline in CD4+ lymphocyte number as well as a qualitative impairment in CD4+ lymphocyte function (Murray et al., N Engl J Med 310:883–889 [1984]; Epstein et al., J Infect Dis 152:727–733 [1985]; and Lane et al., N Engl J Med 313:79–84 [1985]). Immunological abnormalities in helper T cell function occur early, during the asymptomatic phase of infection and prior to the loss in CD4+ cell number (Miedema et al., J Clin Invest 82:1908–1914 [1988]; Laurence et al., J Clin Invest 83:1843–1848 [1989]; and Clerici et al., Nature 339:383 [1989]). Loss of T cell function in vitro predicts both progression to AIDS and survival time (Roos et al., J Infect Dis 171:531–536 [1994]; and Dolan et al., J Infect Dis 172:79–87 [1995]). In addition to these general defects in lymphocyte function, infection typically fails to induce detectable HIV-1-specific proliferative responses (Miedema et al., Immunol Rev 140:35–72 [1994]). When such responses have been observed, they are typically weak, with stimulation indices rarely greater than five (Wharen et al., J Virol 61:2017–2023 [1987]; Berzofsky et al., Nature 334:706–708 [1988]; Krowka et al., J Clin Invest 83:1198–1203 [1989]; Schrier et al., J Immunol 142:1166–1176 [1989]; Schwartz et al., AIDS Res Hum Retro 10:1703–1711 [1994]; and Pontesilli et al., AIDS Res Hum Retro 10:113–114 [1994]).

SUMMARY OF THE INVENTION

This invention relates to the discovery that a strong virus-specific helper T cell proliferative response negatively correlates with viral loads in HIV-1-infected individuals. The finding of a negative correlation between helper T cell responses and viral loads is surprising since previous studies have failed to identify strong proliferative responses in infected persons. The observation of a negative correlation between helper T cell responses and viral loads therefore provides a more useful correlate of immunity to and control of HIV infection than provided by other measures of virus-specific immunity, and suggests that a robust helper T cell response may help control viral proliferation. In addition, the present inventors have discovered specific peptide sequences within the HIV-1 (BH10 clone) p24 capsid protein which contain significant helper T cell epitopes, and which therefore are useful for inducing a protective HIV antiviral helper T cell response.

Accordingly, the invention features a method of producing an HIV-specific helper T cell response in an animal (e.g., a mammal such as a primate, especially a human) by (1) providing at least one polypeptide 8 to 50 amino acid residues in length and having at least one T cell epitope (and potentially a plurality of epitopes) of peptide 112 (SEQ ID NO:2), 117 (SEQ ID NO:3), 118 (SEQ ID NO:10) 120 (SEQ ID NO:4), 121 (SEQ ID NO:7), 122 (SEQ ID NO:5), 125 (SEQ ID NO:6), or 127 (SEQ ID NO:9), which are described below; and (2) administering to the animal an amount of the polypeptide sufficient to produce the HIV-specific helper T cell response. By "HIV" is meant any primate immunodeficiency virus which is capable of causing an acquired immune deficiency syndrome (AIDS) in a human, including viruses in the HIV-1 and HIV-2 families. A peptide mimetic can be used instead of such a polypeptide.

Alternatively, one can produce an HIV-specific helper T cell response in an animal (e.g., a mammal such as a primate, especially a human) by (1) providing an expression vector (a plasmid or virus, for example) encoding at least one polypeptide 8 to 50 amino acid residues in length and including at least one T cell epitope (and potentially a plurality of epitopes) of peptide 112 (SEQ ID NO:2), 117 (SEQ ID NO:3), 118 (SEQ ID NO:10), 120 (SEQ ID NO:4), 121 (SEQ ID NO:7), 122 (SEQ ID NO:5), 125 (SEQ ID NO:6), or 127 (SEQ ID NO:9); and (2) administering to the animal, or to an antigen presenting cell (APC) of the animal, an amount of the expression vector sufficient to produce the HIV-specific helper T cell response.

Similarly, the invention includes a method of producing an HIV-specific helper T cell response in an animal (e.g., a mammal such as a primate, especially a human) by providing a vaccine containing a polypeptide 8 to 50 amino acid residues in length or a peptide mimetic consisting of at least one helper T cell epitope of peptide 109 (SEQ ID NO:1) and optionally a linker sequence; and administering to the animal an amount of the polypeptide or peptide mimetic sufficient to produce the HIV-specific helper T cell response. By a "linker sequence" is meant a peptide sequence or peptide mimetic sequence intervening between two epitopes within the same polypeptide or peptide mimetic. Such linker sequences can, for example, provide necessary spacing such that either epitope can be presented to helper T cells. A linker sequence does not contain an HIV-specific epitope. Instead of a polypeptide or peptide mimetic, an expression vector encoding at least one polypeptide 8 to 50 amino acid residues in length and consisting of at least one T cell epitope of peptide 109 (SEQ ID NO:1) can be used.

Instead of administering directly to the animal the polypeptides, peptide mimetics, or vectors described above, one can remove T cells from the animal; convert the T cells into stimulated helper T cells by stimulating those T cells ex vivo using the same polypeptides, peptide mimetics, or vectors; and introducing the stimulated helper T cells into the same animal to produce the HIV-specific helper T cell response in the animal.

It is preferred that the above methods be used during chronic infection with HIV. By "chronic infection" is meant that the animal's anti-viral immune response is essentially in equilibrium with viral replication, resulting in little change in HIV viral loads over time.

The invention also includes pharmaceutical compositions containing any of the above-mentioned polypeptides or peptide mimetics and an adjuvant, or any of the above-mentioned vectors and a pharmaceutically acceptable diluent such as saline. The compositions of this invention are useful for parenteral administration, such as intravenous, subcutaneous, intramuscular, and intraperitoneal administration. In addition, the formulations may be administered by inhalation, transmucosally, or orally, especially with peptide mimetics.

The polypeptide or peptide mimetic in the methods or compositions described above can further include a second helper T cell epitope of peptide 109 (SEQ ID NO:1), 112 (SEQ ID NO:2), 117 (SEQ ID NO:3), 118 (SEQ ID NO:10), 120 (SEQ ID NO:4), 121 (SEQ ID NO:7), 122 (SEQ ID NO:5), 125 (SEQ ID NO:6), or 127 (SEQ ID NO:9), which can be the same as or different from the first helper T cell epitope.

The preferred helper T cell response produced by the methods is a $Th_1$-type response. By "$Th_1$-type response" is meant an immune response characterized by increased expression of specific cytokines such as interferon-gamma, tumor necrosis factor-alpha and -beta, interleukin-2, and granulocyte macrophage-colony stimulating factor. A $Th_1$-type response is correlated with delayed type hypersensitivity, macrophage activation, and cytotoxicity. Such responses are reviewed in Paul (editor), *Fundamental Immunology*, 3rd ed., Chapter 20: "T-Cell-Derived Cytokines and Their Receptors", Raven Press (1993).

An adjuvant can be co-administered with the polypeptide or peptide mimetic in the methods of this invention. Examples of adjuvants include, but are not limited to, incomplete Freund's, complete Freund's, and alum; and can contain squalene (e.g., MF59 [Chiron Corp, Emeryville, Calif.], monophospholipid A (e.g., Detox™ [Ribi ImmunoChem Research, Inc., Hamilton, Mont.]), saponins (QS-21 [Cambridge Biotech, Cambridge, Mass.]), non-ionic surfactants (NISV [Proteus, Cheshire, United Kingdom]), tocols (U.S. Pat. No. 5,667,784), biodegradable-biocompatible poly(D,L-lactide-co-glycolide) (U.S. Pat. No. 5,417,986), ISCOMs and/or liposomes.

The expression vector used in the methods of the invention can be incorporated into a delivery vehicle such as a liposome or ISCOM prior to administration to the animal. The vector may be administered by incorporating it into a cell ex vivo, and then introducing the transfected cell into the patient. In addition, the polypeptide optionally includes a protein targeting sequence such as a signal peptide, a glycosyl-phosphatidylinositol [GPI] attachment signal, a transmembrane sequence, or a mitochondrial targeting sequence.

The "HIV viral load" of an animal can be determined by any number of methods known in the art, including, but not limited to, amplification (e.g., by PCR) of HIV proviral DNA, genomic RNA, or the spliced transcripts of HIV. Viral load can be expressed as infectious units, DNA copy number, RNA copy number, or number of virions, all per unit volume.

An "epitope" is a three-dimensional molecular surface which is recognized (i.e., via binding) by an antigen binding site of an antibody or a T cell receptor. A "helper T cell epitope" is an epitope of a molecule which binds to the antigen binding groove of a MHC class II molecule on an antigen presenting cell and elicits an epitope-specific response from a CD4+ helper T cell via the binding of the MHC class II/peptide complex on the antigen presenting cell with the T cell receptor on the helper T cell. Such a response elicited by the helper T cell epitope is defined as a "helper T cell response." A helper T cell response can be demonstrated by the in vitro proliferation protocol described below. When such a protocol is used, a helper T cell response is said to exist when a stimulation index of greater than 2.5, preferably greater than 5, more preferably greater than 10 is observed. An "antigen presenting cell" is any cell which expresses a MHC class II molecule on its surface.

An "adjuvant" is a substance that is incorporated into or is administered simultaneously with the polypeptides and peptide mimetics of this invention. Adjuvants increase the duration or level of the immune response in the animal after administration of the polypeptide or peptide mimetic. An adjuvants can also facilitate delivery of the polypeptide or peptide mimetic into the animal or into specific tissues, cells, or locations throughout the body of the animal.

A "liposome" is a lipidic carrier which can deliver peptides or nucleic acids to APCs. Liposomes are described, for example, in Harding et al., Cell 64:393–401 (1991).

By "immune-stimulating complex" or ISCOM is meant a negatively charged cage-like structure of 30–40 nm in size formed spontaneously on mixing cholesterol and Quil A (saponin). ISCOMS are described, for example, in Mowat et al., Immunology Today 12:383–385 (1991).

By "expression vector" is meant any nucleic acid molecule containing regulatory elements that permit expression of a given coding sequence in an appropriate cell. Expression vectors can be introduced into a cell by means of standard molecular biological techniques. After introduction into the cell, the vector can exist extrachromosomally or become integrated into the host genome.

A "protein targeting sequence" refers to a short amino acid sequence that, when linked to a polypeptide, targets that polypeptide to a specific cellular compartment. Examples include a signal peptide, which targets to the extracellular space; a GPI attachment sequence, which targets to the outer surface of the plasma membrane; a mitochondrial targeting sequence which targets to the mitochondrion; a nuclear localization signal, which targets to the nucleus; a peroxisome targeting sequence which targets to peroxisomes; and an endoplasmic reticulum retention signal, which targets to the endoplasmic reticulum. Such sequences are described, for example, in Alberts et al., 3rd ed., Molecular Biology of the Cell, Chapter 12, pages 551–599 (1995).

A "peptide mimetic" is a non-naturally occurring analog of a peptide which, because of protective groups at one or both ends of the mimetic, or replacement of one or more peptide bonds with non-peptide bonds, is less susceptible to proteolytic cleavage than the peptide itself. For instance, one or more peptide bonds can be replaced with an alternative type of covalent bond (e.g., a carbon—carbon bond or an acyl bond). Where proteolytic degradation of the peptides following injection into the subject is a problem, replacement of a particularly sensitive peptide bond with a non-cleavable alternative bond will make the resulting molecule more stable and thus more useful as a therapeutic. Such bonds, and methods of incorporating them into peptide mimetics, are well known in the art. Peptide mimetics can also incorporate amino-terminal or carboxyl terminal blocking groups such as t-butyloxycarbonyl, acetyl, alkyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl, thereby rendering the mimetic less susceptible to proteolysis. Non-peptide bonds and carboxyl- or amino-terminal blocking groups can be used singly or in combination to render the mimetic less susceptible to proteolysis than the corresponding peptide. When a peptide mimetic contains non-natural amino acid analogs, the term "amino acid residue" refers to an amino acid analog containing the functional side chain of the corresponding naturally occurring amino acid.

Unless otherwise defined, all technical and scientific terms used herein have the same meaning as commonly understood by one of ordinary skill in the art to which this invention belongs. The methods and materials described herein can be used to practice the present invention, although other similar or equivalent methods and material known to one skilled in the art can also be used. All publications, patent applications, patents, and other references mentioned herein are incorporated by reference in their entirety. In case of conflict, the present specification, including definitions, will control. The materials, methods, and examples described herein are illustrative only and not intended to be limiting.

Other features and advantages of the invention will be apparent from the following detailed description, and from the claims.

BRIEF DESCRIPTION OF THE DRAWING

FIGS. 4A, 4B, and 4C are graphs of lymphocyte proliferative responses targeted at various peptides derived from the p24 sequence.

DETAILED DESCRIPTION

A number of HIV-1 p24 peptides that elicit HIV-1-specific helper T cell responses have been identified. Contemplated within the scope of this invention are methods of administering p24 peptides, vectors encoding such peptides, and cells containing such vectors to animals suspected of being infected by HIV.

The peptides were discovered in the course of studying a subset of HIV-1 infected persons who have successfully controlled virus replication in the absence of antiretroviral therapy. Despite infections of up to 18 or more years, these individuals maintain normal CD4+ T cell counts and low to undetectable viral loads, and have no evidence of HIV-1 related disease manifestations (Haynes et al., Science 271:324–328 [1996]). Such individuals with long term non-progressive infection were examined for evidence of CD4+ helper T cell responses directed against HIV-1.

All amino acid sequence numberings are as described in Myers et al., Human Retroviruses and AIDS, 1990: A compilation and analysis of nucleic acid and amino acid sequences (1990).

EXAMPLE 1

Anti-HIV-1 Helper T cell Responses in HIV-1-Infected Individuals.

Initial studies were performed in an HIV-1 infected hemophiliac (subject 161-J) with 18 years of documented seropositivity, a normal CD4+ T cell count, and undetectable viral load (<400 RNA molecules/ml), who had never been treated with antiretroviral agents.

To determine the CTL memory response for this individual, peripheral blood mononuclear cells (PBMC) were cultured at 250 to 16,000 cells per well in 24 replicate wells of a 96-well microtiter plate. To each well, $2.5 \times 10^4$ gamma-irradiated (30Gy) PBMC from an HIV-1 seronegative donor were added, along with CD3-specific monoclonal antibody 12F6 at 0.1 µg/ml. 14 days later, wells were split and assayed for cytotoxicity on $^{51}$Cr labeled autologous B-lymphocytes infected with vaccinia-expressing HIV-1 gene products. The fraction of nonresponding wells was defined as the number of wells in which $^{51}$Cr-release did not exceed the mean plus three standard deviations of the spontaneous release of the 24 control wells, divided by the number of assayed wells. Activated cell frequency was calculated via the maximum likelihood method (de St. Groth, J Immunol Methods 49:1123 [1982]). An extremely vigorous CTL memory response was detected in PBMC from the subject, with a calculated frequency of HIV-1-specific CTL of greater than 1 per 200 PBMC.

Figure 1A:
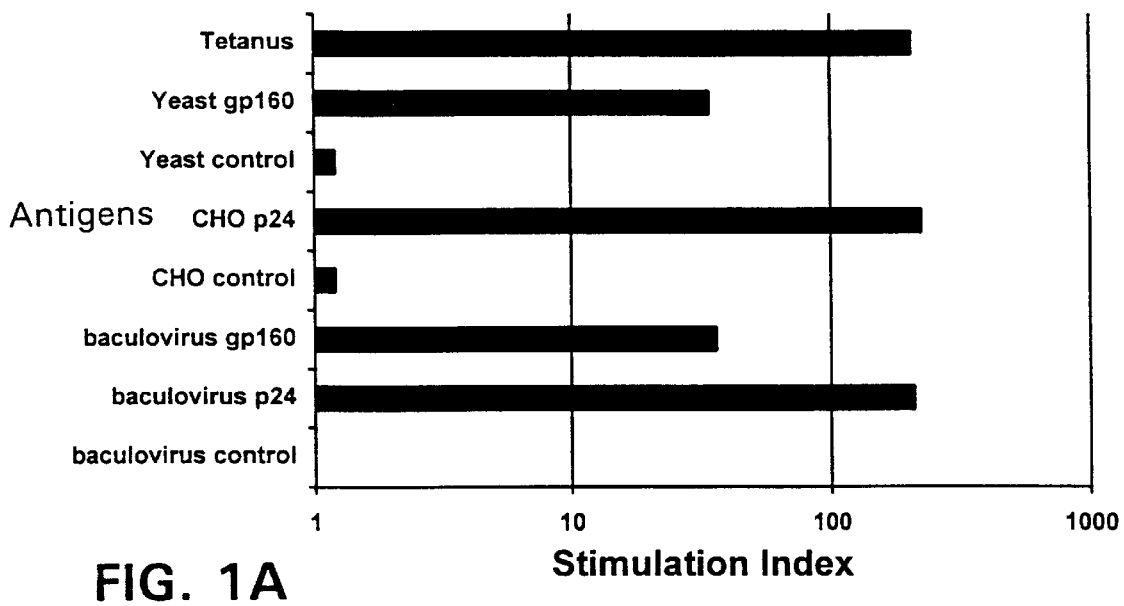
FIGS. 1A and 1B are histograms illustrating HIV-1-specific CD4+ proliferative responses to HIV-1 antigens in one patient.

PBMC from this subject were next examined for evidence of HIV-1-specific lymphocyte proliferative responses. Exposure of freshly isolated PBMC to whole soluble recombinant HIV-1 p24 and gp160proteins resulted in vigorous specific proliferation (FIG. 1A).

The assay for in vitro lymphocyte proliferative response illustrated in FIG. 1A was performed as follows: PBMC were isolated by Ficoll-Hypaque density centrifugation, and tested in a standard [$^3$H]thymidine uptake assay using the designated antigens derived from HIV-1 gp160and p24, as well as control proteins. Proliferation assays were performed by resuspending PBMC in RPMI 1640 medium containing 10% human AB serum, HEPES buffer, L-glutamine, and penicillin-streptomycin. Cells ($1 \times 10^5$ cells/well) were cultured in 6 replicate wells of 96-well "U" bottom plates in the presence of one HIV-1 recombinant protein, control protein, tetanus toxoid, or medium alone. Six days later, cells were pulsed with [$^3$H]thymidine at 1.0 µCi/well, and uptake was measured six hours later with a scintillation counter (Topcount). The HIV-1 p24 protein (Microgenesys, Meriden, Conn.) was derived from HIV-1 strain NY-5, and the HIV-1 gp160 protein (Microgenesys, Meriden, Conn.) was from HIV-1 strain LAV. Both proteins were produced by the manufacturer in a baculovirus expression system and demonstrated 90–95% purity. These proteins were tested over a range of concentrations, with 0.5 µg/ml as the standard concentration. A mixture of baculovirus proteins was used as control antigen at 0.015 μg/ml, which was equal to the non-specific baculovirus protein concentration in the recombinant protein preparations used in the assay. Comparable results were obtained at 1.5 μg/ml of recombinant control protein. Yeast- and CHO-derived recombinant HIV-1 proteins were provided by Chiron Corporation (Emeryville, Calif.). The p24 Gag protein (amino acids 139–369) of HIV-1 strain SF2 was recombinantly derived in a yeast expression system. Gp120 of HIV-1 SF2 was expressed in CHO cells. These proteins were >90% and 94.8% pure, respectively. Each protein was used at a concentration of 0.5 μg/ml; 0.5 μg/ml preparations of CHO and yeast proteins were used as controls. Tetanus toxoid (Connaught) was used at 2 μg/ml. For the recombinant HIV-1 proteins, a stimulation index (SI) was defined as the ratio of the mean counts-per-minute (CPM) of the HIV-1 protein wells to the mean CPM of the control protein wells. For tetanus toxoid, the SI was defined as the ratio of the mean CPM of the tetanus toxoid-stimulated wells to the mean CPM of six control wells containing PBMC and medium alone. For assays using PBMC depleted of CD4+ cells or PBMC depleted of CD8+ cells, PBMC were cultured as described above for the CTL memory experiment in the presence of gamma irradiated (40Gy) autologous PBMC and antigen.

Nearly identical stimulation indices were obtained using HIV-1 antigens derived from baculovirus, yeast, or Chinese hamster ovary (CHO) expression systems, whereas control antigens derived from the same sources elicited no responses. PBMC stimulated with p24 resulted in vigorous lymphocyte proliferation, with stimulation indices of greater than 200 for both baculovirus- and CHO-derived HIV-1 p24 antigens. Both baculovirus- and yeast-derived gp160 elicited a less intense but significant lymphocyte proliferative response as compared to that elicited by p24.

Figure 1B:
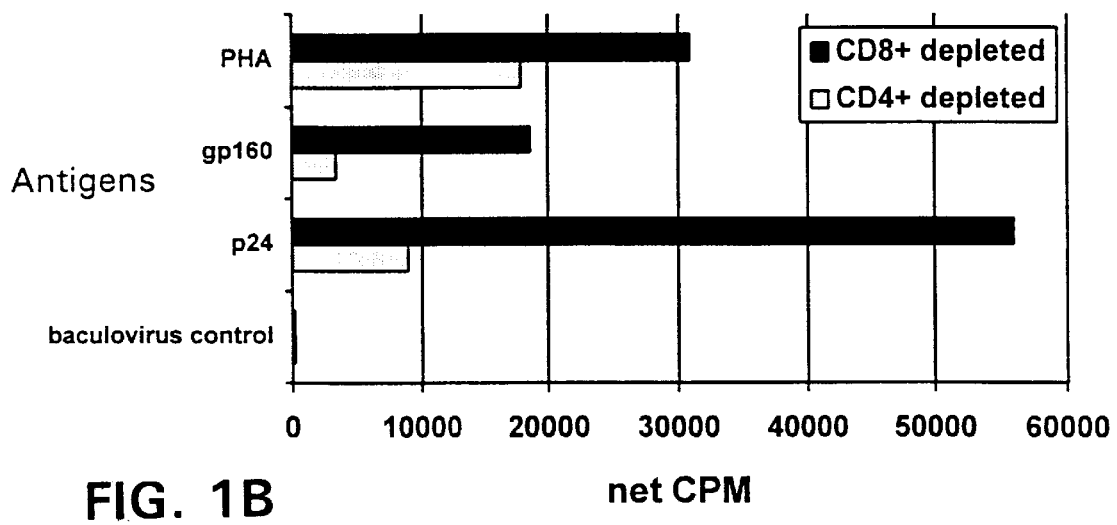

To show that HIV-1-specific proliferation was mediated by the CD4+ lymphocyte subset, aliquots of PBMC from the same subject were depleted of either the CD8+ or CD4+ fraction, using antibody-coated flasks according to manufacturer's instructions (Applied Immune Sciences, Menlo Park Calif.), and tested for proliferation in the presence of HIV-1 antigens as described above. Efficiencies of CD8+ and CD4+ depletions were 94.7% and 89.3%, respectively. The results are shown in FIG. 1B.

These virus specific proliferative responses were highly reproducible over a two year period of observation of the subject, indicating that such responses can persist in the absence of detectable viremia and in the absence of disease progression. The presence of such responses in a cohort of individuals with a wide range of viral loads was next examined.

Ten HIV-1 infected individuals with varying clinical histories and viral loads who had never been treated with antiretroviral therapy were evaluated. This cohort included four long-term nonprogressors as well as six persons having different durations of chronic infection. In those subjects with an undetectable viral load, a value of 400 viral RNA copies/ml (minimum detectable level) was assigned. Subjects participating in this study were all documented to be HIV-1 positive by HIV-1/-2 enzyme immunoassay (EIA), which was confirmed by Western Blot. Each individual signed an informed consent agreement approved by the Massachusetts General Hospital institutional review board. Patient designations, CD4 counts, and genomic viral RNA loads for the 10 subjects were:

DF-2851, 243 cells/mm$^3$, 503,000 copies/ml;
PJ-9202, 80 cells/mm$^3$, 485,000 copies/ml;
JH-5300, 507 cells/mm$^3$, 279,000 copies/ml;
MK-099, 420 cells/mm$^3$, 58,228 copies/ml;
PG-9011, 1400 cells/mm$^3$, 2,950 copies/ml;
MK-089, 1099 cells/mm$^3$, 2,396 copies/ml;
CTS-01, 900 cells/mm$^3$, 700 copies/ml;
BD-0971, 599 cells/mm$^3$, <400 copies/ml;
LS-5175, 1738 cells/mm$^3$, <400 copies/ml; and
161-J, 1400 cells/mm$^3$, <400 copies/ml.

Figure 2:
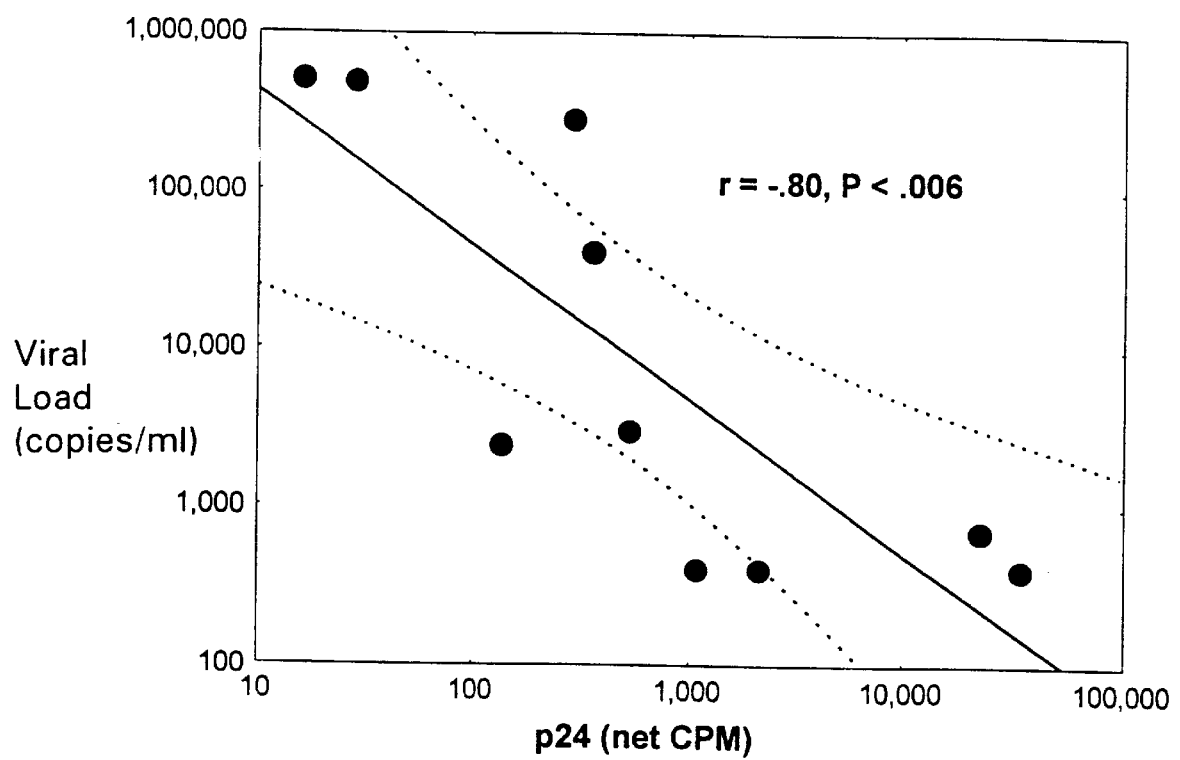
FIG. 2 is a graph of p24-specific CD4+ lymphocyte proliferation versus viral load.

The relationship between viral load and proliferative response to p24 antigen was examined, and found to demonstrate a highly significant inverse correlation (FIG. 2). Assays were performed as described for the data in FIGS. 1A and 1B. The relationship was examined using linear regression performed with Statistica software package (Statsoft Inc., Tulsa, Okla.). The solid line in FIG. 2 represents the regression line, and the dotted line represents the 95% confidence interval for the regressed line.

Individuals with the strongest p24-specific proliferative responses had the lowest viral loads, and those individuals with higher HIV-1 viral loads had a markedly decreased ability to respond to p24 ($R=-0.80$, $P<0.006$). For eight of the individuals evaluated, assays were repeated on a second visit, and the results were similar. Surprisingly, comparison of proliferative responses to Env protein and viral load failed to show a correlation, but significant Env-specific responses were seen in persons with low viral loads.

To ensure that the observed CD4+ T cell responses were not just reflective of the duration of infection, a long-term non-progressor with a high viral load was evaluated. This subject had documented HIV-1 infection for over ten years, a CD4 cell count of 900 cells/mm$^3$, and a viral load of 175,000 RNA molecules/ml plasma. In this individual, the stimulation index with respect to p24 and gp160 antigen remained at <2.5 even nine months after the viral load was reduced to undetectable levels (<400 copies/ml) in plasma following initiation of combination antiretroviral therapy. No evidence of HIV-1-specific proliferative responses (mean SI=1.8) to either p24 or gp160 were detected in fifteen seronegative lab workers, and no responses were detected in twenty individuals who had been repeatedly exposed sexually to HIV-1 but remain uninfected.

Figure 3A:
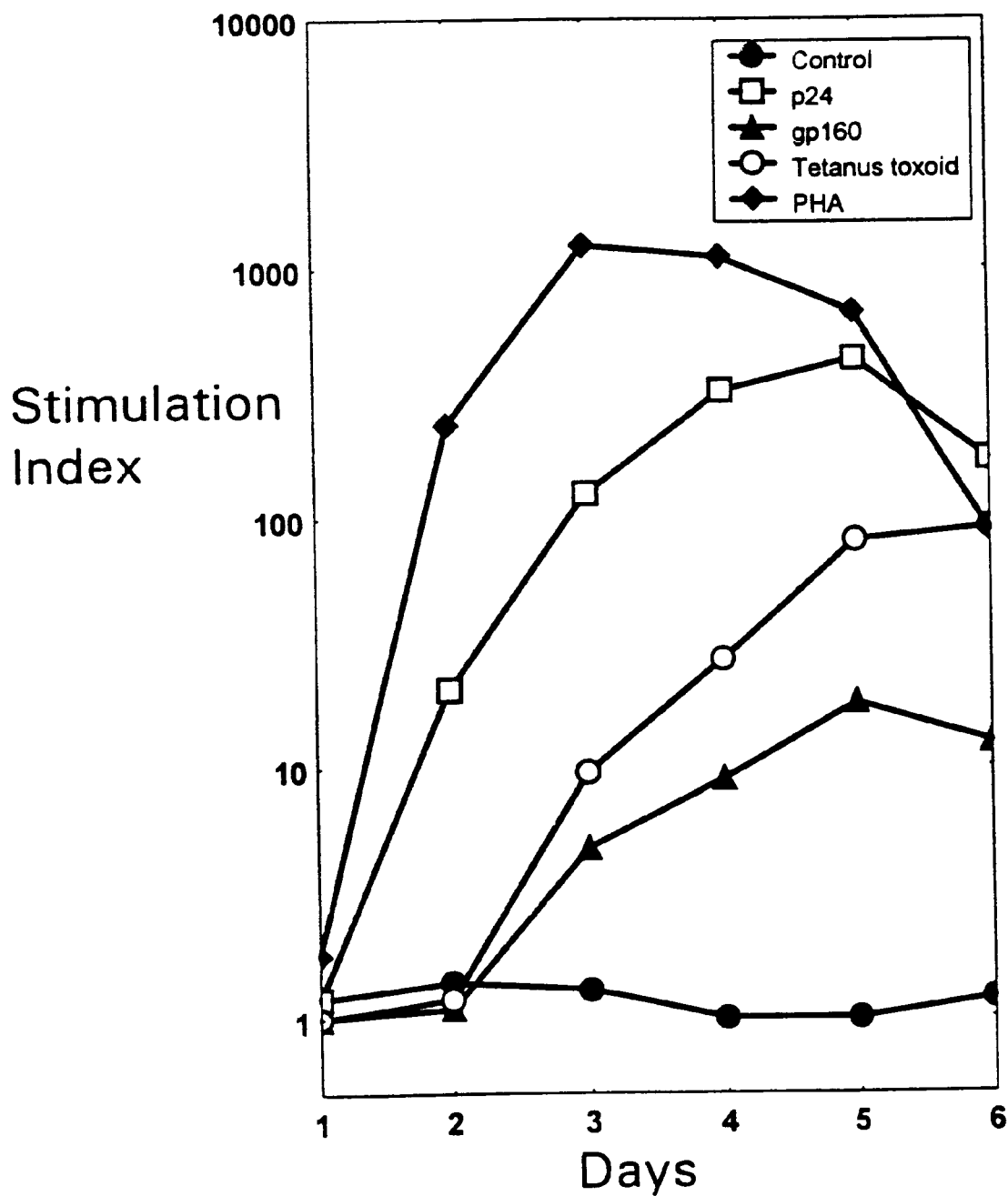
FIGS. 3A, 3B, and 3C are graphs of the kinetics of HIV-1-specific proliferative responses.
Figure 3B:
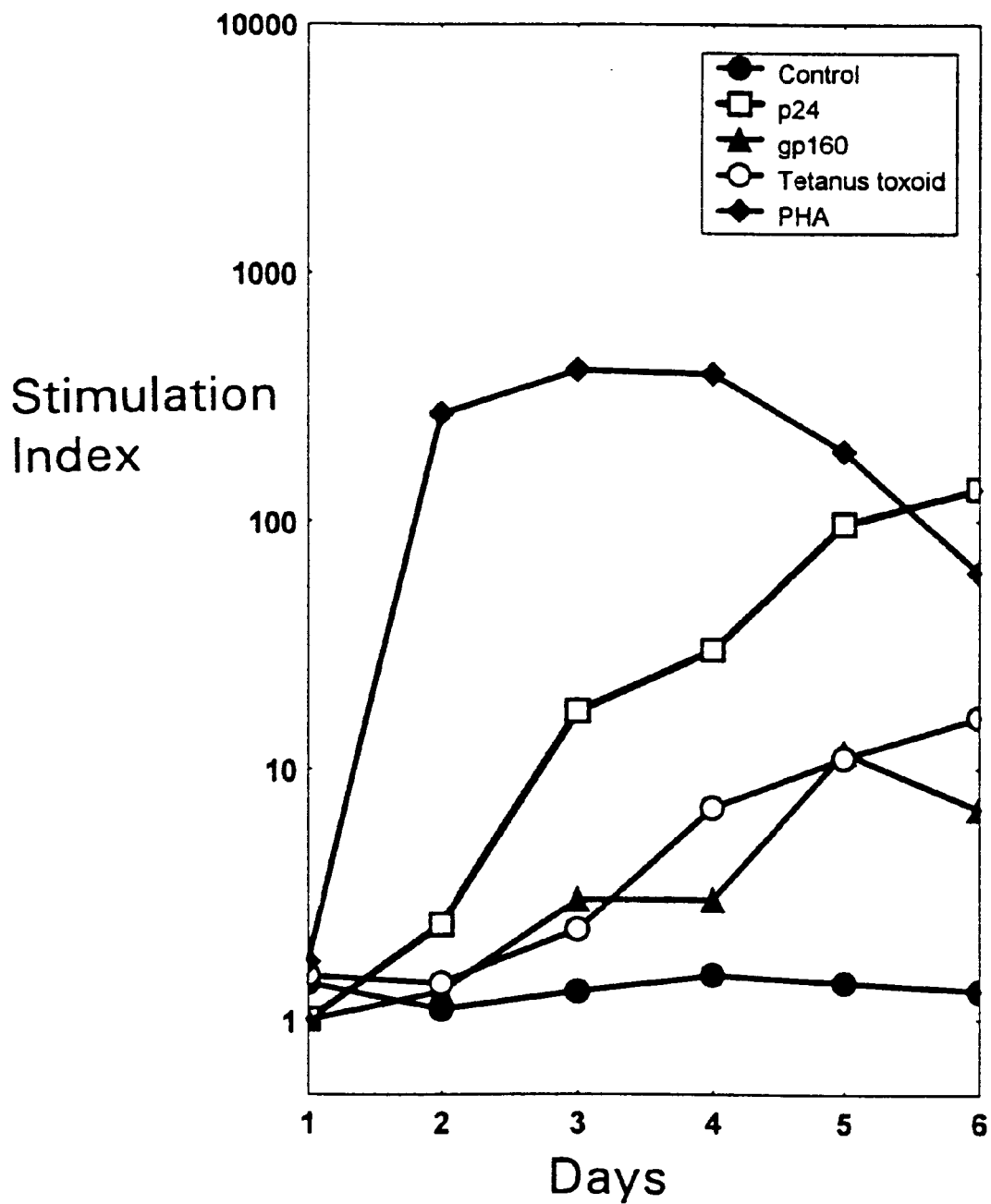

To further characterize the HIV-1 specific lymphocyte responses, the in vitro kinetics of lymphocyte proliferation over a six day period in two persons with robust anti-HIV-1 responses were examined (FIGS. 3A and 3B).

FIGS. 3A and 3B are graphs of the in vitro kinetics of T cell proliferation for subjects 161-J and CTS-01, respectively. Proliferation assays were performed as described above, and harvested every 24 hours. Subject 161-J was described above. Subject CTS-01 is a male infected sexually with HIV-1 who never has been treated with antiretroviral therapy. This patient has documented asymptomatic infection for 14 years, an HIV-1 viral load of 700 RNA copies/ml, and a CD4 count of 900 cells/mm$^3$.

Figure 3C:
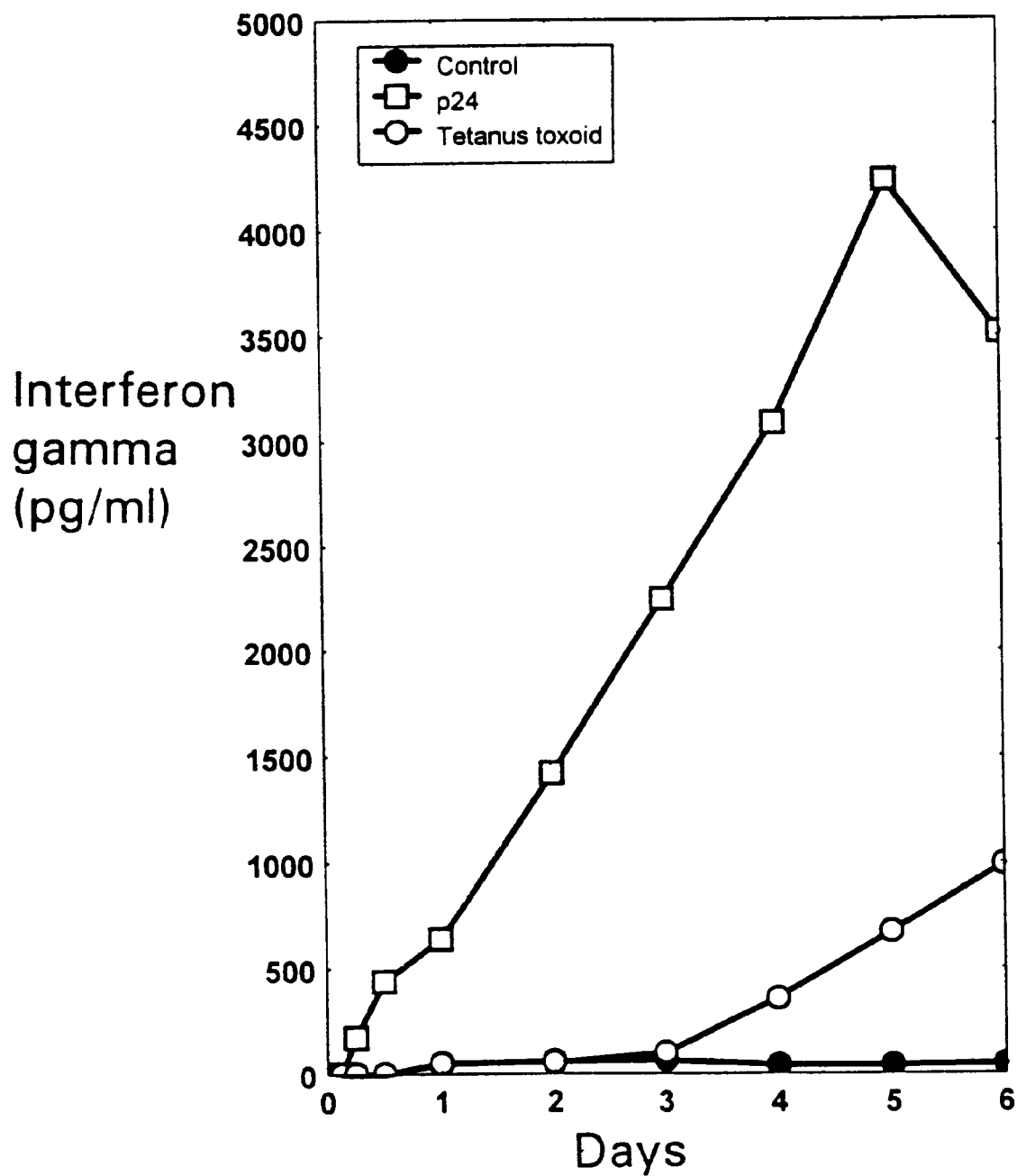
Figure 3D:
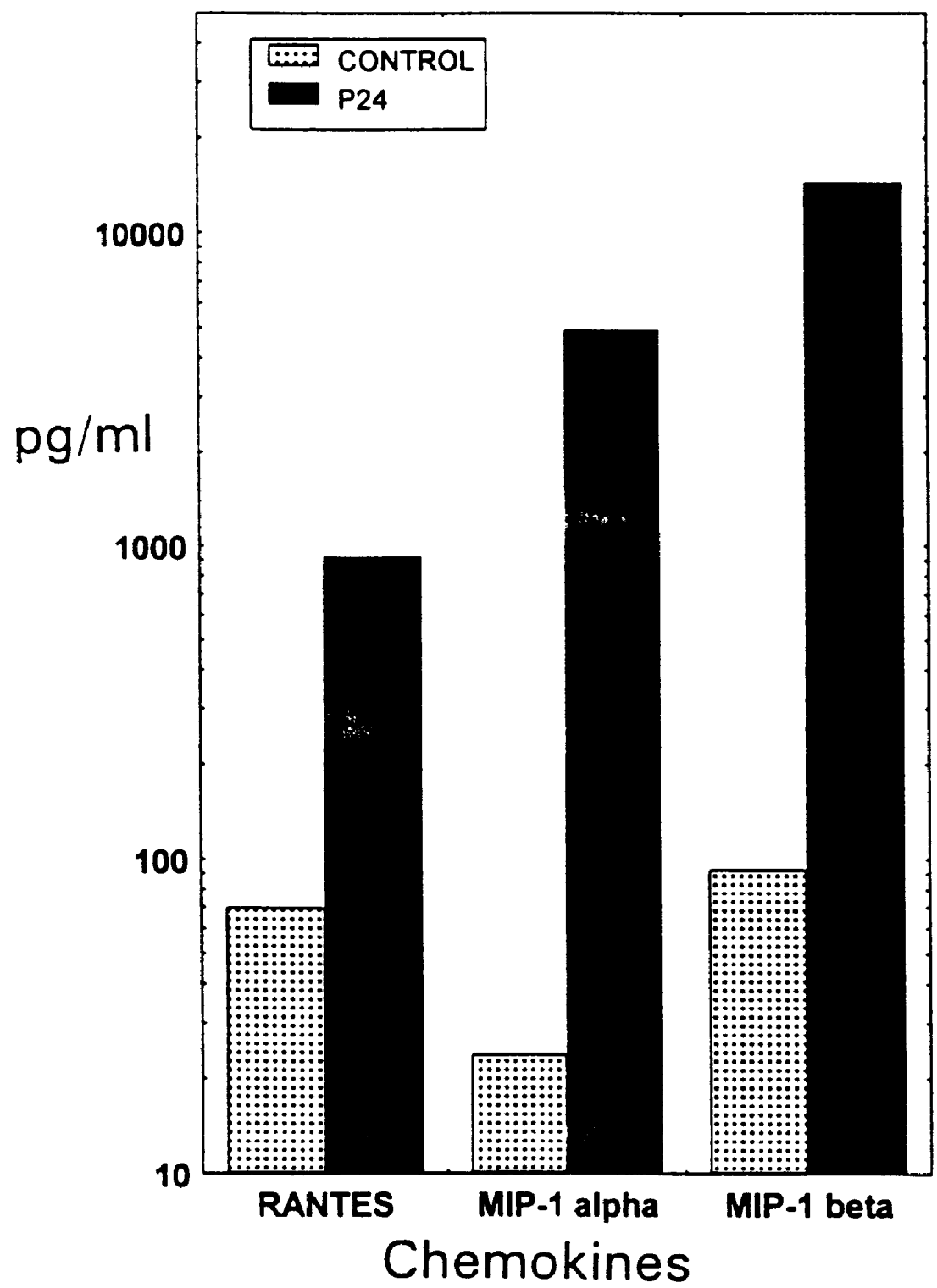
FIG. 3D is a graph of chemokine production from the HIV-1-specific proliferative cells of an HIV-positive individual.

Both subjects demonstrated vigorous proliferative responses to p24 and gp160. Lymphocyte proliferation assays were performed as described above. Concentration of p24 was titrated to determine the lowest amount of antigen required to stimulate a p24-specific lymphocyte proliferative response. For subject 161-J, a p24 concentration as low as 0.05 μg/ml elicited a response, whereas for subject CTS-01, the response was lost at concentrations <0.5 μg/ml. Exposure to HIV-1 antigen resulted in the specific induction of interferon gamma production (FIG. 3C). In vitro kinetics of interferon gamma cytokine production were determined by stimulating PBMC from subject 161-J as described above and harvesting cell supernatants at 3, 6, 12, and 24 hours on day 1 and every 24 hours for days 2–6. Cell culture supernatants were frozen at −70° C., thawed and analyzed by ELISA (Endogen) for the presence of interferon-gamma according to the manufacturer's instructions. Similarly, stimulation with viral antigen resulted in the production of RANTES, MIP-1α and MIP-1β in day 6 cell culture supernatants (FIG. 3D), as determined by ELISA kits (R&D Systems). Proliferative responses to HIV-1 antigen were abrogated with the addition of 100 ng/ml of rIL-10.

Figure 4B:
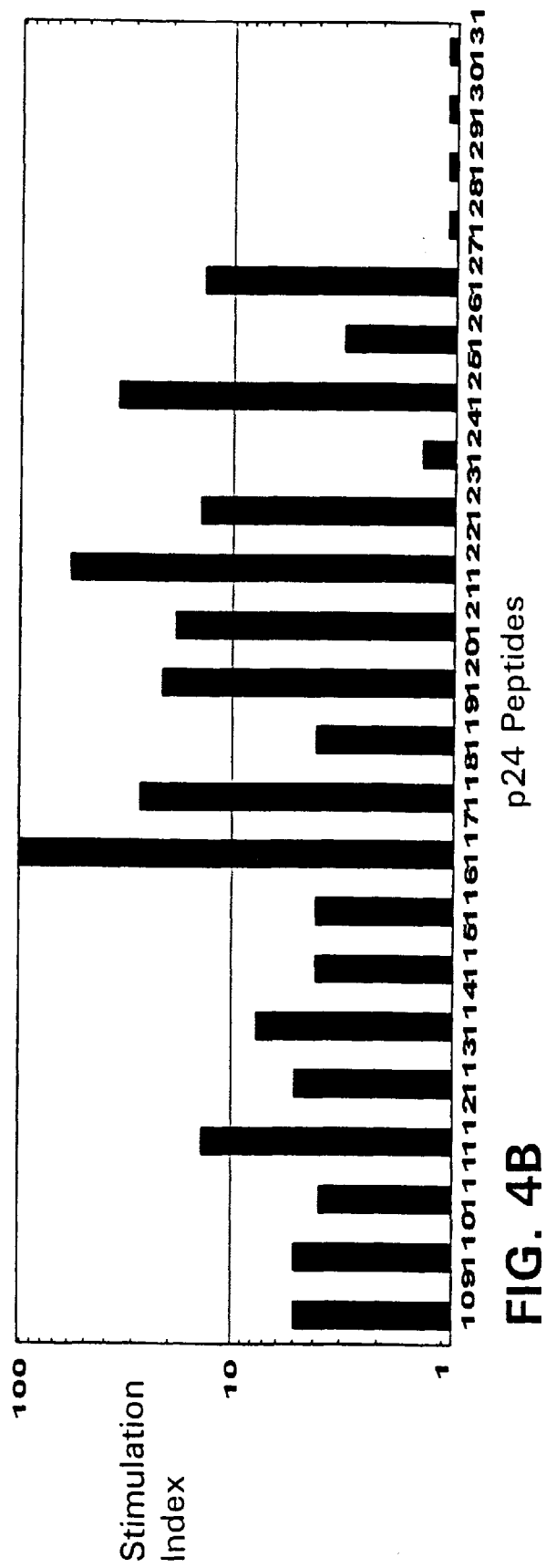
Figure 4C:
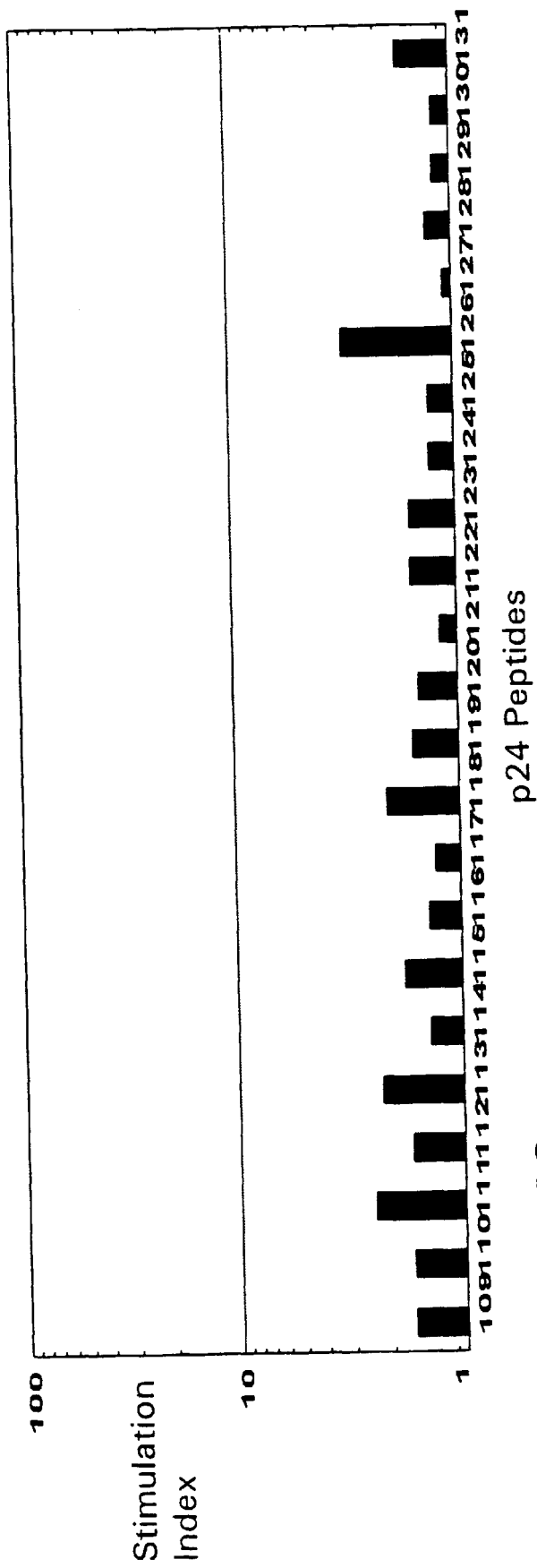

Two individuals with strong p24-specific helper T cell responses were further characterized to determine the dominant epitopes targeted (FIGS. 4A–4C). PBMC from subjects 161-J (FIG. 4A) and CTS-01 (FIG. 4B), as well as a HIV-1 seronegative control (FIG. 4C), were stimulated in vitro with synthetic p24 peptides. The synthetic HIV-1 p24 peptides were 22 amino acids in length and span the entire p24 protein of the clone BH10 GAG precursor protein (amino acids 133–377 of GAG, see Johnson et al., J Immunol 147:1512–1521 [1991]). The BH10 p24 sequence is as follows:

```
Pro Ile Val Gln Asn Leu Gln Gly Gln Met Val His Gln
Ala Leu
Ser Pro Arg Thr Leu Asn Ala Trp Val Lys Val Ile Glu
Glu Lys
Ala Phe Ser Pro Glu Val Ile Pro Met Phe Ser Ala Leu
Ser Glu
Gly Ala Thr Pro Gln Asp Leu Asn Thr Met Leu Gln Thr
Val Gly
Gly His Gln Ala Ala Met Gln Met Leu Lys Glu Thr Ile
Asn Glu
Glu Ala Ala Glu Trp Asp Arg Leu His Pro Val His Ala
Gly Pro
Ile Ala Pro Gly Gln Met Arg Glu Pro Arg Gly Ser Asp
Ile Ala
Gly Thr Thr Ser Thr Leu Gln Glu Gln Ile Ala Trp Met
Thr Gln
Gln Pro Pro Ile Pro Val Gly Glu Ile Tyr Lys Arg Trp
Ile Ile
Leu Gly Leu Asn Lys Ile Val Arg Met Tyr Ser Pro Val
Ser Ile
Leu Asp Ile Arg Gln Gly Pro Lys Glu Pro Phe Arg Asp
Tyr Val
Asp Arg Phe Tyr Lys Thr Leu Arg Ala Glu Gln Ala Thr
Gln Glu
Val Lys Asn Trp Met Thr Glu Thr Leu Leu Val Gln Asn
Ala Asn
Pro Asp Cys Lys Thr Ile Leu Lys Ala Leu Gly Pro Gly
Ala Thr
Leu Glu Asp Met Met Thr Ala Cys Gln Gly Val Gly Gly
Pro Gly
His Lys Ala Arg Val Leu (SEQ ID NO:8)
```

Each peptide overlaps the adjacent peptide by 12 amino acids. The peptides were used at 1 μg/ml, and proliferation assays were harvested and measured for [³H]thymidine incorporation on day 6. Peptide-specific responses were conservatively defined as having an SI>10. Dominant responses were detected to peptide 109 (amino acids 133–154; Pro Ile Val Gln Asn Ile Gln Gly Gln Met Val His Gln Ala Ile Ser Pro Arg Thr Leu Asn Ala; SEQ ID NO:1; SI=83) in subject 161-J and to peptide 117 (amino acids 213–234; Asp Arg Val His Pro Val His Ala Gly Pro Ile Ala Pro Gly Gln Met Arg Glu Pro Arg Gly Ser; SEQ ID NO:3; SI=102) in subject CTS-01, confirming the presence of virus specific proliferative responses and demonstrating that multiple epitopes are targeted. Some peptides stimulated helper T cells from both individuals (peptides 112 [amino acids 163–184; Ala Phe Ser Pro Glu Val Ile Pro Met Phe Ser Ala Leu Ser Glu Gly Ala Thr Pro Gln Asp Leu; SEQ ID NO:2], 118 [amino acids 223–244; Ile Ala Pro Gly Gln Met Arg Glu Pro Arg Gly Ser Asp Ile Ala Gly Thr Thr Ser Thr Leu Gln; SEQ ID NO:10], 120 [amino acids 243–264; Leu Gln Glu Gln Ile Gly Trp Met Thr Asn Asn Pro Pro Ile Pro Val Gly Glu Ile Tyr Lys Arg; SEQ ID NO:4], and 122 [amino acids 263–284; Lys Arg Trp Ile Ile Leu Gly Leu Asn Lys Ile Val Arg Met Tyr Ser Pro Thr Ser Ile Leu Asp; SEQ ID NO:5]), whereas other peptides eliciting an SI of 10 or greater were differentially recognized. Peptides 121 (amino acids 253–274; Asn Pro Pro Ile Pro Val Gly Glu Ile Tyr Lys Arg Trp Ile Ile Leu Gly Leu Asn Lys Ile Val; SEQ ID NO:7), 125 (amino acids 293–314; Phe Arg Asp Tyr Val Asp Arg Phe Tyr Lys Thr Leu Arg Ala Glu Gln Ala Ser Gln Glu Val Lys; SEQ ID NO:6), and 127 (amino acids 313–334; Val, Lys, Asn, Trp Met Thr Glu Thr Leu Leu Val Gln Asn Ala Asn Pro Asp Cys Lys Thr Ile Leu; SEQ ID NO:9) also significantly stimulated T cells both individuals, although the SI induced by these peptides were less than 10. For both subjects, whole protein generated higher stimulation indices than did any individual peptide, consistent with the polyclonal nature of the response. No significant proliferative responses to HIV-1 peptides were detected in HIV-1 seronegative control subjects (FIG. 1C).

These data demonstrate that, in infected persons who control viremia, HIV-1 induces a vigorous CD4+ T cell proliferative response targeted at multiple viral epitopes, and that these responses are weak or absent in persons with progressive infection and higher viral loads. These data thus establish a correlate of protective immunity.

The effect of antiviral therapy on the HIV-1-specific proliferative response in primary infection was next examined in order to determine if inhibiting viral replication early in the course of infection would allow generation of this response.

Figure 5A:
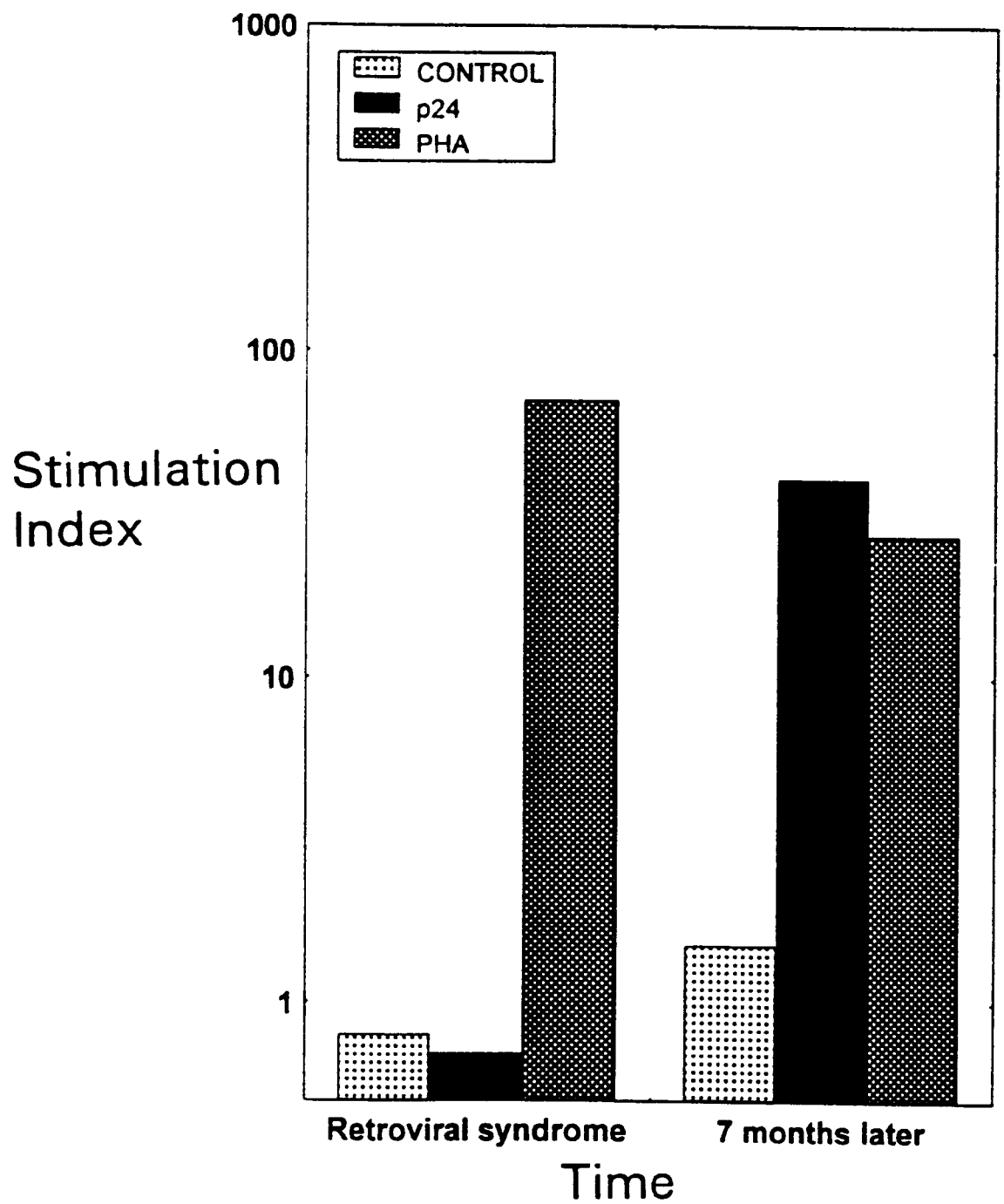
FIGS. 5A, 5B, and 5C are graphs comparing patients' HIV-1-specific proliferative responses before and after combination antiretroviral therapy.
Figure 5B:
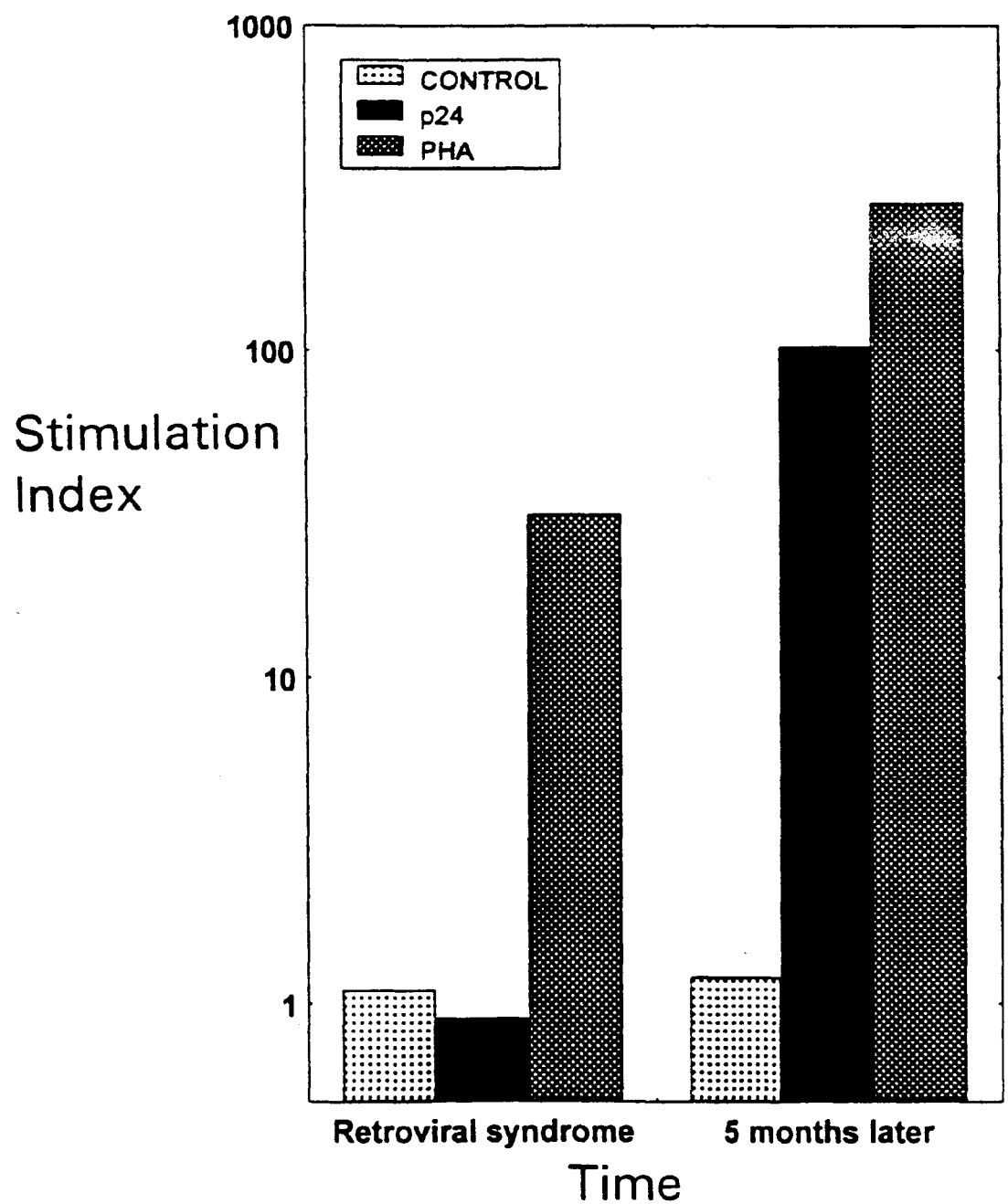
Figure 5C:
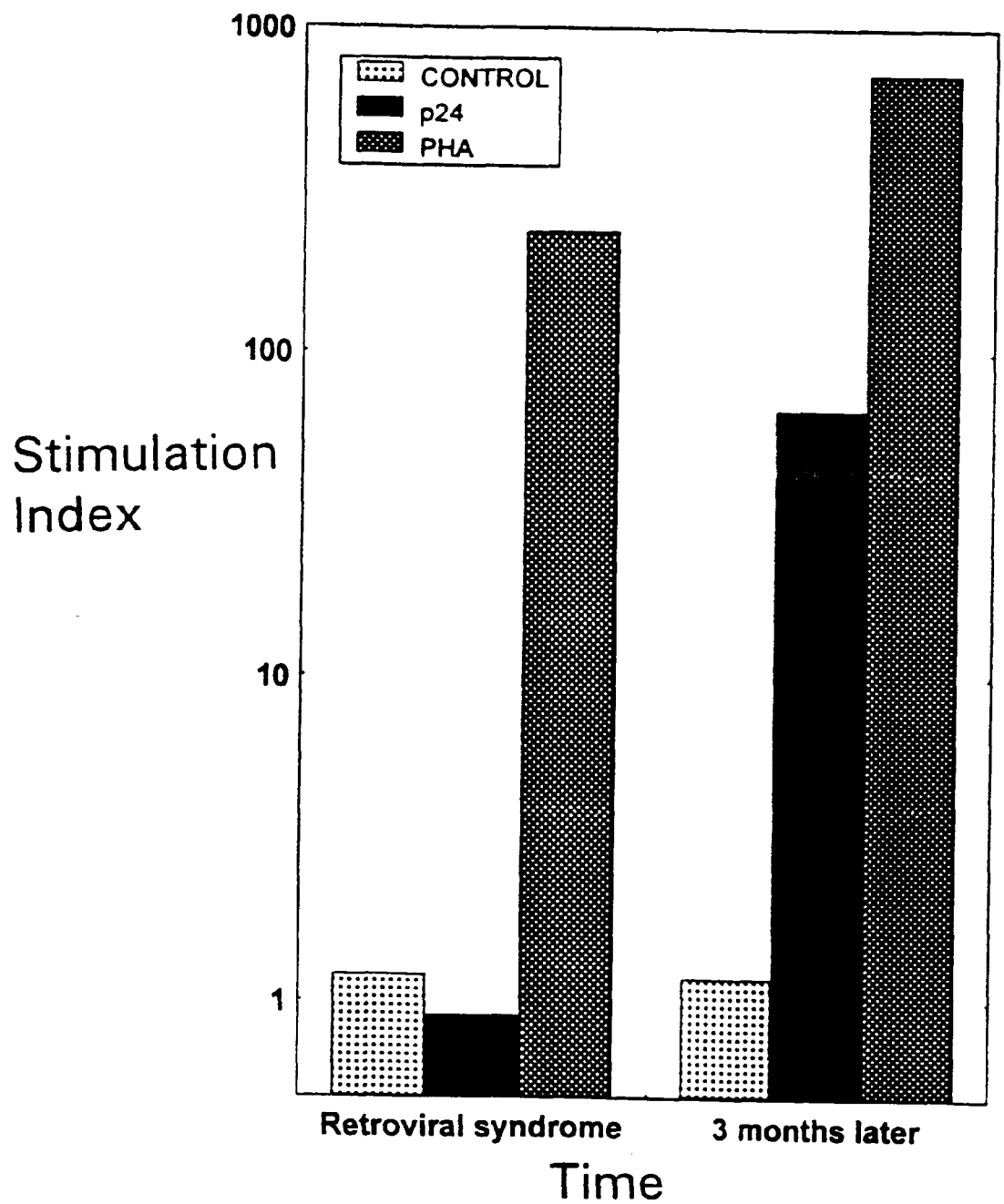

FIGS. 5A–5C are graphs of the results from lymphocyte proliferation assays for three individuals diagnosed with primary HIV-1 infection and acute retroviral syndrome. All individuals began treatment with three drug combination therapy (including a protease inhibitor) at the time of diagnosis and had viral loads <400 copies/ml within 2 months of initiating therapy. The diagnosis was made on the basis of a negative HIV-1/-2 EIA (Abbott laboratories), and the presence of HIV-1 viral RNA (Amplicor HIV Monitor Test, Roche Molecular Systems, Branchberg, N.J.) and subsequent seroconversion documented by both HIV-1/-2 EIA and Western blot (Abbott Laboratories). Proliferation assays were performed at baseline (prior to initiation of antiviral therapy) and at frequent intervals while on therapy, using baculovirus-derived p24 antigen at 5 μg/ml.

Figure 5D:
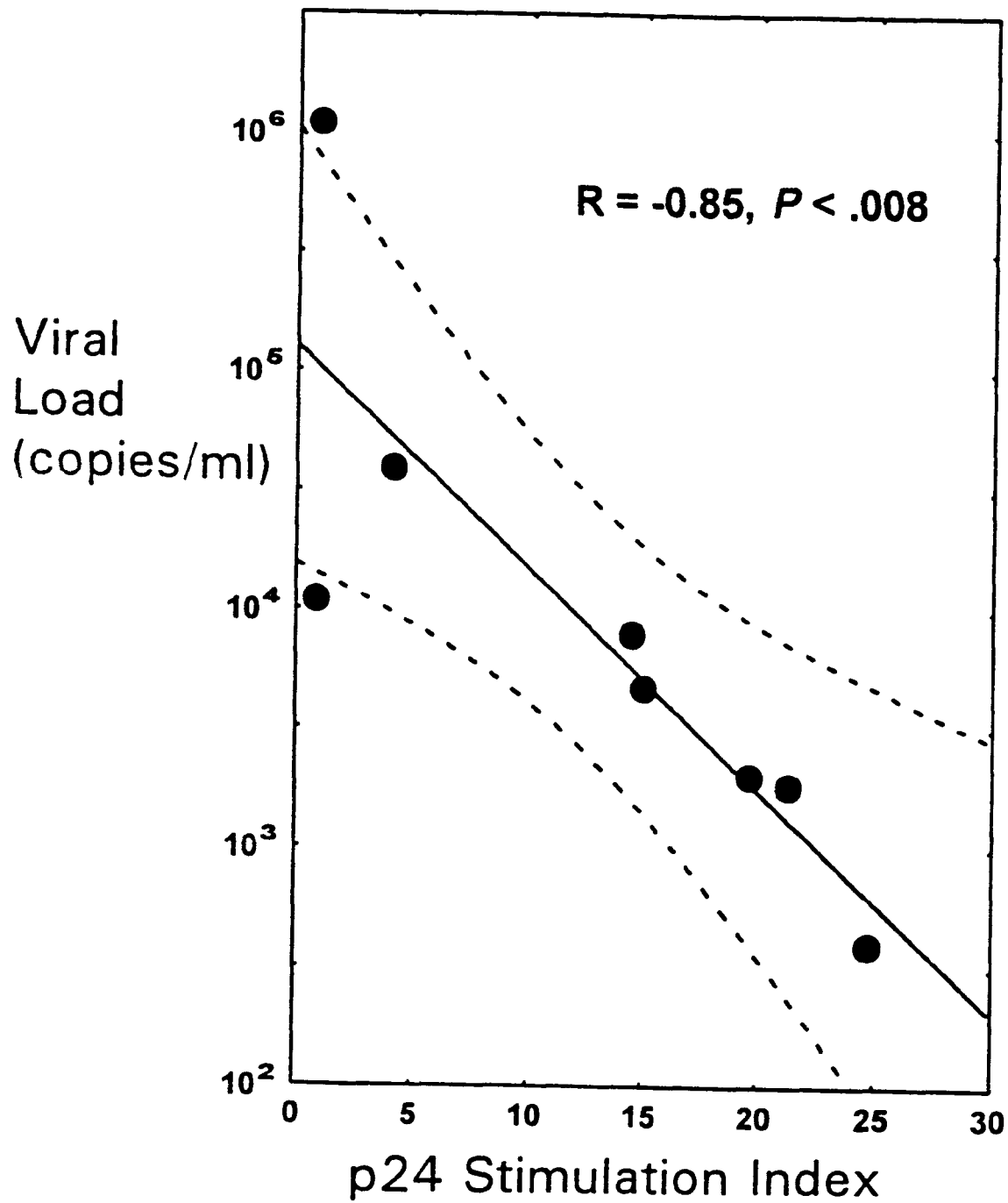
FIG. 5D is graph of p24-specific CD4+ lymphocyte proliferation versus viral load.

With the initiation of aggressive antiviral therapy, the lowering of plasma viral load was strongly correlated to the generation of a p24-specific proliferative response (FIG. 5D, P<0.008, R=−0.85). These results contrast with the reported lack of strong HIV-1-specific proliferative responses following initiation of potent antiviral therapy in chronic infection (Kellerher et al., J Infect Dis 173:321–329 [1996] and Schnittman et al., AIDS Res Hum Retro 13:815–818 [1997]) and with the lack of detectable responses in a person tested 6 months after seroconversion who was not treated with antiviral therapy (see patient JH-5300 in de St. Groth et al., Id.). No untreated patients identified at the time of primary infection were available as additional controls because all patients chose to follow recommendations to initiate antiviral therapy.

These data provide firm evidence that HIV-1 induces a strong HIV-1-specific proliferative response in persons who are controlling viremia in the absence of antiretroviral therapy, and suggest that early, aggressive treatment of primary infection may facilitate generation of these responses. Although disease progression in HIV-1 infection is likely to be multi-factorial, the inverse correlation between p24-specific CD4+ T cell proliferative responses and viral load are consistent with the hypothesis that these responses contribute to immunological control of virus replication. This hypothesis is supported by animal models of chronic viral infection, which have shown that the presence of functional CD4+ cells is essential for the maintenance of effective immunity during chronic infection (Battegay et al., J Virol 68:4700–4704 [1994]; Matloubian et al., J Virol 68:8056–8063 [1994]; Von Herrath et al., J Virol 70:1072–1079 [1996]; Thomsen et al., J Immunol 157:3074–3080 [1996]; and Planz et al., Proc Natl Acad Sci USA 94:6874–6879 [1997]).

Understanding the correlates of immune protection in HIV-1 infection is critical to the design of immunotherapeutic interventions and vaccines. The data presented provide evidence for the importance of HIV-1-specific helper T cell responses, particularly those targeted towards T cell epitopes contained in p24 peptides 109, 112, 117, 118, 122, 125, and 127.

EXAMPLE 2

Liposomal Delivery of Peptides

The peptides used in the methods of this invention can be delivered encapsulated in liposomes, which are lipidic particles containing cationic and neutral lipids. Liposomes have been successfully used as drug carriers and more recently in safe and potent adjuvant strategies for malaria vaccination in humans (Fries et al., Proc Natl Acad Sci USA 89:358 [1992]). Liposomes have been shown to incorporate soluble proteins and deliver these antigens to cells for both in vitro and in vivo $CD8^+$ mediated CTL response (Reddy et al., J Immunol 148:1585–1589 [1992]; and Collins et al., J Immunol 148:3336–3341 [1992]). Thus, liposomes may be used as a vehicle for delivering synthetic peptides into APCs. Harding et al. (Cell 64, 393–401 [1991]) have demonstrated that the targeting of liposome-delivered antigen to either of two intracellular class II-loading compartments, early endosomes and/or lysosomes, can be accomplished by varying the membrane composition of the liposome: acid-sensitive liposomes were found to target their contents to early endosomes, while acid-resistant liposomes were found to deliver their contents to lysosomes. Thus, the peptides of the invention can be incorporated into acid-sensitive liposomes where delivery to endosomes is desired, and into acid-resistant liposomes for delivery to lysosomes.

Liposomes are prepared by standard detergent dialysis or dehydration-rehydration methods. For acid-sensitive liposomes, dioleoylphosphatidylethanolamine (DOPE) and palmitoylhomocystein (PHC) may be utilized, while dioleoylphospatidylcholine (DOPC) and dioleoylphosphatidylserine (DOPS) may be used for the preparation of acid-resistant liposomes. $10^{-5}$ mol of total lipid (DOPC/DOPS or DOPE/PHC at 4:1 mol ratios) are dried, hydrated in 0.2 ml of HEPES buffered saline (HBS) (150 Mm NaCl, 1 mM EGTA, 10 mM HEPES pH 7.4), and sonicated. The lipid suspensions are solubilized by the addition of 0.1 ml of 1 M octylglucoside in HBS. The peptides to be entrapped are added to 0.2 ml of 0.6 mM lipid in 20% HBS. The mixture is then frozen, lyophilized overnight, and rehydrated. These liposomes may be treated with chymotrypsin to digest any surface-bound peptide.

Human immunization can be carried out under the protocol approved by both The Johns Hopkins University Joint Committee for Clinical Investigation and the Human Subject Research Review Board of the Office of the Surgeon General of the U.S. Army (Fries et al., Proc Natl Acad Sci USA 89:358–362 [1992]), using dosages described in the above-cited literature for liposome-based delivery of therapeutic agents.

For example, a formulation consisting of 630 µg of peptide 117, 2.2 mg of monophosphoryl lipid A, 25.4 mg of dimyristoyl phophatidylcholine, 2.9 mg of dimyristoyl phosphatidylglycerol, 13 mg of cholesterol, and saline in 1 ml total volume is injected intramuscularly into the deltoid of an individual. A booster shot is given at 8–12 weeks after the first immunization, and a second booster is given at 16–20 weeks, using the same formulation. PBMC from the individual can be taken before and after each of the three immunizations for measuring the helper T cell response to peptide 117. Additional boosters can be given as needed. By varying the amount of peptide or lipid composition, the immunization protocol can be optimized for eliciting a maximal helper T cell response.

If the individual is HIV-1 positive prior to the vaccination, the vaccine would be considered therapeutically effective if (1) the individual's viral load fails to increase as rapidly as would be expected in the absence of the vaccine; (2) the individual's helper T cell response or CD4+ cell count increases significantly by the end of the vaccination series; (3) the severity, duration, or number of the individual's opportunistic infections is decreased; or (4) the expected life-span of the individual is increased.

EXAMPLE 3

ISCOM Delivery of Peptides

Alternatively, the p24 peptides of the methods of this invention can be administered as ISCOMs. Protective immunity has been generated in a variety of experimental models of infection, including toxoplasmosis and Epstein-Barr virus-induced tumors, using ISCOMS as the delivery vehicle for antigens (Mowat et al., Immunology Today 12:383–385 [1991]). Doses of antigen as low as 1 µg encapsulated in ISCOMS have been found to produce class I mediated CTL responses (Takahashi et al., Nature 344:873–875 [1990]). Peptides are delivered into cells using ISCOMS in a manner and dosage similar to that described above for liposomes.

EXAMPLE 4

Delivery of Vectors Encoding Peptides

Another way to introduce a HIV p24 peptide into a patient is by overexpressing within the cells of the patient a nucleic acid construct which includes expression control sequences operably linked to a sequence encoding the peptide. Since the peptides do not contain a methionine start codon, such a codon is included as part of the expression control sequences. The nucleic acid construct is a non-replicating linear or circular DNA or RNA vector, or an autonomously replicating plasmid or viral vector; or the construct is integrated into the host genome. Any vector that can transfect a mammalian cell may be used in the methods of the invention. Methods for constructing expression vectors are well known in the art (see, e.g., *Molecular Cloning: A Laboratory Manual*, Sambrook et al., eds., Cold Spring Harbor Laboratory, 2nd Edition, Cold Spring Harbor, N.Y., 1989).

In these vectors, a suitable promoter is operably linked to the nucleic acid sequence encoding the peptide. Any promoter that can direct a high level of transcription initiation in the target cells (e.g., APCs) may be used in the invention. Non-tissue specific promoters, such as the cytomegalovirus (DeBernardi et al., Proc Natl Acad Sci USA 88:9257–9261 [1991], and references therein), mouse metallothionine I (Hammer et al., J Mol Appl Gen 1:273–288 [1982]), HSV thymidine kinase (McKnight, Cell 31:355–365 [1982]), and SV40 early (Benoist et al., Nature 290:304–310 [1981]) promoters may be used in methods of the invention, as overexpression of peptides in the methods of the invention would not be expected to adversely affect transfected cells. The above-described nucleic acid constructs and vectors can be introduced into target cells in vivo or in vitro by any standard method: e.g., as naked DNA (Donnelly et al., Annu Rev Immunol 15:617–648 [1997]), incorporated into ISCOMS, liposomes, or erythrocyte ghosts, or by biolistic transfer, calcium precipitation, or electroporation. Alternatively, one can employ a viral-based vector as a means for introducing the nucleic acid into the cells of the animal. Preferred viral vectors include those derived from replication-defective hepatitis viruses (e.g., HBV and HCV), retroviruses (see, e.g., WO89/07136; and Rosenberg et al., N Eng J Med 323 (9):570–578 [1990]), adenovirus (see, e.g., Morsey et al., J Cell Biochem, Supp. 17E [1993]), adeno-associated virus (Kotin et al., Proc Natl Acad Sci USA 87:2211–2215 [1990]), replication defective herpes simplex viruses (HSV; Lu et al., Abstract, page 66, Abstracts of the Meeting on Gene Therapy, Sep. 22–26, 1992, Cold Spring Harbor Laboratory, Cold Spring Harbor, N.Y.), canary pox virus, and any modified versions of these vectors. Cells transfected in vitro (e.g., APCs obtained from the patient) can be cultured and cloned, if desired, prior to introduction into the patient.

EXAMPLE 5

Ex Vivo stimulation of Helper T cells

Instead of administering the peptide, peptide mimetic, or vector directly to the patient, one can remove helper T cells from the patient; stimulate those T cells ex vivo using the same peptide, peptide mimetic, or vector; and introduce the stimulated helper T cells into the same patient.

For example, 50 ml of whole blood from a patient chronically infected with HIV-1 is drawn, and the PBMC isolated by standard ficoll methods. The PBMC are stimulated with an effective amount of the peptide, peptide mimetic, or expression vector previously described. The effective amount of peptide, peptide mimetic, or vector can be easily determined by one skilled in the art. Vector-transfected cells can be cultured and cloned, if desired. After several days of ex vivo stimulation, the helper T cells are introduced back into the animal through an intravenous line.

What is claimed is:

1. A method of producing an HIV-specific helper T cell response in an animal, comprising the steps of:
   (a) providing a polypeptide 8 to 50 amino acid residues in length, said polypeptide comprising a helper T cell epitope of peptide 112 (SEQ ID NO:2), 117 (SEQ ID NO:3), 118 (SEQ ID NO:10), 120 (SEQ ID NO:4), 121 (SEQ ID NO:7), 122 (SEQ ID NO:5), 125 (SEQ ID NO:6), or 127 (SEQ ID NO:9); and
   (b) administering to the animal an amount of the polypeptide sufficient to produce the HIV-specific helper T cell response.

2. The method of claim 1, further comprising administering to the animal an anti-retroviral drug.

3. The method of claim 1, wherein the HIV-specific helper T cell response is a Th$_1$-type response.

4. The method of claim 1, wherein the polypeptide comprises a plurality of helper T cell epitopes derived from the capsid protein of HIV.

5. The method of claim 1, wherein the polypeptide comprises a helper T cell epitope of peptide 112 (SEQ ID NO:2).

6. The method of claim 1, wherein the polypeptide comprises a helper T cell epitope of peptide 117 (SEQ ID NO:3).

7. The method of claim 1, wherein the polypeptide comprises a helper T cell epitope of peptide 120 (SEQ ID NO:4).

8. The method of claim 1, wherein the polypeptide comprises a helper T cell epitope of peptide 122 (SEQ ID NO:5).

9. The method of claim 1, wherein an adjuvant is administered with the polypeptide.

10. The method of claim 1, wherein the polypeptide is incorporated into a liposome or ISCOM prior to administration to the animal.

11. The method of claim 1, wherein the animal is a human.

12. The method of claim 1, further comprising administering a second polypeptide 8 to 50 amino acid residues in length, said second polypeptide comprising a second helper T cell epitope of peptide 109 (SEQ ID NO:1), 112 (SEQ ID NO:2), 117 (SEQ ID NO:3), 118 (SEQ ID NO:10), 120 (SEQ ID NO:4), 121 (SEQ ID NO:7), 122 (SEQ ID NO:5), 125 (SEQ ID NO:6), or 127 (SEQ ID NO:9), said second helper T cell epitope being different from said first helper T cell epitope.

13. The method of claim 1, wherein said polypeptide further comprises a second helper T cell epitope of peptide 109 (SEQ ID NO:1), 112 (SEQ ID NO:2), 117 (SEQ ID NO:3), 118 (SEQ ID NO:10), 120 (SEQ ID NO:4), 121 (SEQ ID NO:7), 122 (SEQ ID NO:5), 125 (SEQ ID NO:6), or 127 (SEQ ID NO:9).

14. A method of producing an HIV-specific helper T cell response in an animal, comprising the steps of:
   (a) providing a peptide mimetic, said peptide mimetic comprising a helper T cell epitope of peptide 109 (SEQ ID NO:1), 112 (SEQ ID NO:2), 117 (SEQ ID NO:3), 118 (SEQ ID NO:10), 120 (SEQ ID NO:4), 121 (SEQ ID NO:7), 122 (SEQ ID NO:5), 125 (SEQ ID NO:6), or 127 (SEQ ID NO:9); and
   (b) administering to the animal an amount of the peptide mimetic sufficient to produce the HIV-specific helper T cell response.

15. The method of claim 14, wherein said peptide mimetic further comprises a second helper T cell epitope of peptide 109 (SEQ ID NO:1), 112 (SEQ ID NO:2), 117 (SEQ ID NO:3), 118 (SEQ ID NO:10), 120 (SEQ ID NO:4), 121 (SEQ ID NO:7), 122 (SEQ ID NO:5), 125 (SEQ ID NO:6), or 127 (SEQ ID NO:9).

16. A method of producing an HIV-specific helper T cell response in an animal, comprising the steps of:
   (a) providing a polypeptide 8 to 50 amino acid residues in length, said polypeptide being selected from the group consisting of (1) peptide 109 (SEQ ID NO:1); (2) a head-to-tail dimer of peptide 109, the monomers being optionally linked by a linker sequence; (3) a fragment of peptide 109 comprising a helper T cell epitope; and (4) a head-to-tail multimer of said fragment, each fragment being optionally linked to the adjacent one by a linker sequence; and
   (b) administering to the animal an amount of the polypeptide sufficient to produce the HIV-specific helper T cell response.

17. A method of producing an HIV-specific helper T cell response in an animal, comprising the steps of:
   (a) providing a peptide mimetic, said peptide mimetic being selected from the group consisting of (1) a mimetic of peptide 109 (SEQ ID NO:1); (2) a head-to-tail dimer of the mimetic of peptide 109, the monomers being optionally linked by a linker sequence; (3) a fragment of the mimetic of peptide 109 comprising a helper T cell epitope; and (4) a head-to-tail multimer of said fragment, each fragment being optionally linked to the adjacent one by a linker sequence; and
   (b) administering to the animal an amount of the peptide mimetic sufficient to produce the HIV-specific helper T cell response.

18. A method of producing an HIV-specific helper T cell response in an animal, comprising the steps of:
   (a) providing T cells obtained from the animal;
   (b) converting the T cells into stimulated helper T cells by stimulating the T cells in vitro with a polypeptide 8 to 50 amino acid residues in length, said polypeptide comprising a helper T cell epitope of peptide 112 (SEQ ID NO:2), 117 (SEQ ID NO:3), 118 (SEQ ID NO:10), 120 (SEQ ID NO:4), 121 (SEQ ID NO:7), 122 (SEQ ID NO:5), 125 (SEQ ID NO:6), or 127 (SEQ ID NO:9); and (c) introducing the stimulated helper T cells into the animal, thereby producing the HIV-specific helper T cell response.

19. The method of claim 18, wherein said polypeptide further comprises a second helper T cell epitope of peptide 109 (SEQ ID NO:1), 112 (SEQ ID NO:2), 117 (SEQ ID NO:3), 118 (SEQ ID NO:10), 120 (SEQ ID NO:4), 121 (SEQ ID NO:7), 122 (SEQ ID NO:5), 125 (SEQ ID NO:6), or 127 (SEQ ID NO:9).

20. A method of producing an HIV-specific helper T cell response in an animal, comprising the steps of:

(a) providing T cells obtained from the animal;

(b) converting the T cells into stimulated helper T cells by stimulating the T cells in vitro with a peptide mimetic, said peptide mimetic comprising a helper T cell epitope of peptide 109 (SEQ ID NO:1), 112 (SEQ ID NO:2), 117 (SEQ ID NO:3), 118 (SEQ ID NO:10), 120 (SEQ ID NO:4), 121 (SEQ ID NO:7), 122 (SEQ ID NO:5), 125 (SEQ ID NO:6), or 127 (SEQ ID NO:9); and (c) introducing the stimulated helper T cells into animal, thereby producing the HIV-specific helper T cell response.

21. The method of claim 20, wherein said peptide mimetic further comprises a helper T cell epitope of peptide 109 (SEQ ID NO:1), 112 (SEQ ID NO:2), 117 (SEQ ID NO:3), 118 (SEQ ID NO:10), 120 (SEQ ID NO:4), 121 (SEQ ID NO:7), 122 (SEQ ID NO:5), 125 (SEQ ID NO:6), or 127 (SEQ ID NO:9).

22. A method of producing an HIV-specific helper T cell response in an animal, comprising the steps of:

(a) providing T cells obtained from the animal;

(b) converting the T cells into stimulated helper T cells by stimulating the T cells in vitro with a polypeptide 8 to 50 amino acid residues in length, said polypeptide being selected from the group consisting of (1) peptide 109 (SEQ ID NO:1); (2) a head-to-tail dimer of peptide 109, the monomers being optionally linked by a linker sequence; (3) a fragment of peptide 109 comprising a helper T cell epitope; and (4) a head-to-tail multimer of said fragment, each fragment being optionally linked to the adjacent one by a linker sequence; and (c) introducing the stimulated helper T cells into the animal, thereby producing the HIV-specific helper T cell response.

23. A method of producing an HIV-specific helper T cell response in an animal, comprising the steps of:

(a) providing T cells obtained from the animal;

(b) converting the T cells into stimulated helper T cells by stimulating the T cells in vitro with a peptide mimetic, said peptide mimetic being selected from the group consisting of (1) a mimetic of peptide 109 (SEQ ID NO:1); (2) a head-to-tail dimer of the mimetic of peptide 109, the monomers being optionally linked by a linker sequence; (3) a fragment of the mimetic of peptide 109 comprising a helper T cell epitope; and (4) a head-to-tail multimer of said fragment, each fragment being optionally linked to the adjacent one by a linker sequence; and (c) introducing the stimulated helper T cells in the animal, thereby producing the HIV-specific helper T cell response.

24. A composition comprising (a) a polypeptide 8 to 50 amino acid residues in length, said polypeptide comprising a helper T cell epitope of peptide 112 (SEQ ID NO:2), 117 (SEQ ID NO:3), 118 (SEQ ID NO:10), 120 (SEQ ID NO:4), 121 (SEQ ID NO:7), 122 (SEQ ID NO:5), 125 (SEQ ID NO:6), or 127 (SEQ ID NO:9); and (b) an adjuvant.

25. The composition of claim 24, wherein said polypeptide further comprises a helper T cell epitope of peptide 109 (SEQ ID NO:1), 112 (SEQ ID NO:2), 117 (SEQ ID NO:3), 118 (SEQ ID NO:10), 120 (SEQ ID NO:4), 121 (SEQ ID NO:7), 122 (SEQ ID NO:5), 125 (SEQ ID NO:6), or 127 (SEQ ID NO:9).

26. A composition comprising (a) a polypeptide 8 to 50 amino acid residues in length, said polypeptide being selected from the group consisting of (1) peptide 109 (SEQ ID NO:1); (2) a head-to-tail dimer of peptide 109, the monomers being optionally linked by a linker sequence; (3) a fragment of peptide 109 comprising a helper T cell epitope; and (4) a head-to-tail multimer of said fragment, each fragment being optionally linked to the adjacent one by a linker sequence; and (b) an adjuvant.

27. The method of claim 1, wherein the animal is chronically infected with HIV.

28. The method of claim 1, wherein the polypeptide comprises a helper T cell epitope of peptide 121 (SEQ ID NO:7).

29. The method of claim 1, wherein the polypeptide comprises a helper T cell epitope of peptide 125 (SEQ ID NO:6).

30. The method of claim 1, wherein the polypeptide comprises a helper T cell epitope of peptide 127 (SEQ ID NO:9).

31. A method of producing an HIV-specific helper T cell response in an animal, comprising the steps of:

(a) providing a polypeptide 8 to 50 amino acid residues in length, said polypeptide comprising a helper T cell epitope of HIV capsid, wherein the helper T cell epitope produces a stimulation index greater than 10 in CD4+ cells in a person who is chronically infected with HIV; and (b) administering to the animal an amount of the polypeptide sufficient to produce the HIV-specific helper T cell response.

32. The method of claim 1, wherein the polypeptide comprises a helper T cell epitope of peptide 118 (SEQ ID NO:10).

33. The method of claim 1, further comprising administering to the animal a second drug.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 22 amino acids
      (B) TYPE: amino acid
      (D) TOPOLOGY: linear (ii) MOLECULE TYPE: peptide (xi) SEQUENCE DESCRIPTION: SEQ ID NO:1:

Pro Ile Val Gln Asn Ile Gln Gly Gln Met Val His Gln Ala Ile Ser
 1          5               10            15

Pro Arg Thr Leu Asn Ala
        20

(2) INFORMATION FOR SEQ ID NO:2:

(i) SEQUENCE CHARACTERISTICS:
      (A) LENGTH: 22 amino acids
      (B) TYPE: amino acid
      (D) TOPOLOGY: linear (ii) MOLECULE TYPE: peptide (xi) SEQUENCE DESCRIPTION: SEQ ID NO:2:

Ala Phe Ser Pro Glu Val Ile Pro Met Phe Ser Ala Leu Ser Glu Gly
 1          5               10            15

Ala Thr Pro Gln Asp Leu
        20

(2) INFORMATION FOR SEQ ID NO:3:

(i) SEQUENCE CHARACTERISTICS:
      (A) LENGTH: 22 amino acids
      (B) TYPE: amino acid
      (D) TOPOLOGY: linear (ii) MOLECULE TYPE: peptide

```
     (xi) SEQUENCE DESCRIPTION: SEQ ID NO:3:

Asp Arg Val His Pro Val His Ala Gly Pro Ile Ala Pro Gly Gln Met
1               5                  10                  15

Arg Glu Pro Arg Gly Ser
            20

(2) INFORMATION FOR SEQ ID NO:4:

(i) SEQUENCE CHARACTERISTICS:
         (A) LENGTH: 22 amino acids
         (B) TYPE: amino acid
         (D) TOPOLOGY: linear (ii) MOLECULE TYPE: peptide (xi) SEQUENCE DESCRIPTION: SEQ ID NO:4:

Leu Gln Glu Gln Ile Gly Trp Met Thr Asn Asn Pro Pro Ile Pro Val
1               5                  10                  15

Gly Glu Ile Tyr Lys Arg
            20

(2) INFORMATION FOR SEQ ID NO:5:

(i) SEQUENCE CHARACTERISTICS:
         (A) LENGTH: 22 amino acids
         (B) TYPE: amino acid
         (D) TOPOLOGY: linear (ii) MOLECULE TYPE: peptide (xi) SEQUENCE DESCRIPTION: SEQ ID NO:5:

Lys Arg Trp Ile Ile Leu Gly Leu Asn Lys Ile Val Arg Met Tyr Ser
1               5                  10                  15

Pro Thr Ser Ile Leu Asp
            20

(2) INFORMATION FOR SEQ ID NO:6:

(i) SEQUENCE CHARACTERISTICS:
         (A) LENGTH: 22 amino acids
         (B) TYPE: amino acid
         (D) TOPOLOGY: linear (ii) MOLECULE TYPE: peptide (xi) SEQUENCE DESCRIPTION: SEQ ID NO:6:

Phe Arg Asp Tyr Val Asp Arg Phe Tyr Lys Thr Leu Arg Ala Glu Gln
1               5                  10                  15

Ala Ser Gln Glu Val Lys
            20

(2) INFORMATION FOR SEQ ID NO:7:

(i) SEQUENCE CHARACTERISTICS:
         (A) LENGTH: 22 amino acids
         (B) TYPE: amino acid
         (D) TOPOLOGY: linear (ii) MOLECULE TYPE: peptide (xi) SEQUENCE DESCRIPTION: SEQ ID NO:7:

Asn Pro Pro Ile Pro Val Gly Glu Ile Tyr Lys Arg Trp Ile Ile Leu
1               5                  10                  15

Gly Leu Asn Lys Ile Val
            20
```

(2) INFORMATION FOR SEQ ID NO:8:

(i) SEQUENCE CHARACTERISTICS:
        (A) LENGTH: 231 amino acids
        (B) TYPE: amino acid
        (D) TOPOLOGY: linear (ii) MOLECULE TYPE: protein (xi) SEQUENCE DESCRIPTION: SEQ ID NO:8:

```
Pro Ile Val Gln Asn Leu Gln Gly Gln Met Val His Gln Ala Leu Ser
 1               5                  10                  15

Pro Arg Thr Leu Asn Ala Trp Val Lys Val Ile Glu Glu Lys Ala Phe
             20                  25                  30

Ser Pro Glu Val Ile Pro Met Phe Ser Ala Leu Ser Glu Gly Ala Thr
         35                  40                  45

Pro Gln Asp Leu Asn Thr Met Leu Gln Thr Val Gly Gly His Gln Ala
     50                  55                  60

Ala Met Gln Met Leu Lys Glu Thr Ile Asn Glu Glu Ala Ala Glu Trp
 65                  70                  75                  80

Asp Arg Leu His Pro Val His Ala Gly Pro Ile Ala Pro Gly Gln Met
                 85                  90                  95

Arg Glu Pro Arg Gly Ser Asp Ile Ala Gly Thr Thr Ser Thr Leu Gln
            100                 105                 110

Glu Gln Ile Ala Trp Met Thr Gln Gln Pro Pro Ile Pro Val Gly Glu
        115                 120                 125

Ile Tyr Lys Arg Trp Ile Ile Leu Gly Leu Asn Lys Ile Val Arg Met
    130                 135                 140

Tyr Ser Pro Val Ser Ile Leu Asp Ile Arg Gln Gly Pro Lys Glu Pro
145                 150                 155                 160

Phe Arg Asp Tyr Val Asp Arg Phe Tyr Lys Thr Leu Arg Ala Glu Gln
                165                 170                 175

Ala Thr Gln Glu Val Lys Asn Trp Met Thr Glu Thr Leu Leu Val Gln
            180                 185                 190

Asn Ala Asn Pro Asp Cys Lys Thr Ile Leu Lys Ala Leu Gly Pro Gly
        195                 200                 205

Ala Thr Leu Glu Asp Met Met Thr Ala Cys Gln Gly Val Gly Gly Pro
    210                 215                 220

Gly His Lys Ala Arg Val Leu
225                 230
```

(2) INFORMATION FOR SEQ ID NO:9:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:9:

```
Val Lys Asn Trp Met Thr Glu Thr Leu Leu Val Gln Asn Ala Asn Pro
 1               5                  10                  15

Asp Cys Lys Thr Ile Leu
             20
```

(2) INFORMATION FOR SEQ ID NO:10:

(i) SEQUENCE CHARACTERISTICS:
        (A) LENGTH: 22 amino acids (B) TYPE: amino acid
        (D) TOPOLOGY: linear (ii) MOLECULE TYPE: peptide (xi) SEQUENCE DESCRIPTION: SEQ ID NO:10:

Ile Ala Pro Gly Gln Met Arg Glu Pro Arg Gly Ser Asp Ile Ala Gly
 1               5                  10                  15

Thr Thr Ser Thr Leu Gln
             20